US007250502B2

(12) United States Patent
Cregg

(10) Patent No.: US 7,250,502 B2
(45) Date of Patent: Jul. 31, 2007

(54) FORMALDEHYDE DEHYDROGENASE GENES FROM METHYLOTROPHIC YEASTS

(75) Inventor: James M. Cregg, Claremont, CA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 270 days.

(21) Appl. No.: 10/459,970

(22) Filed: Jun. 12, 2003

(65) Prior Publication Data

US 2003/0215920 A1    Nov. 20, 2003

Related U.S. Application Data

(62) Division of application No. 09/345,828, filed on Jul. 2, 1999, now Pat. No. 6,730,499.

(60) Provisional application No. 60/091,699, filed on Jul. 3, 1998.

(51) Int. Cl.
C07H 21/04 (2006.01)
C12N 15/00 (2006.01)
C12N 1/00 (2006.01)
C12N 1/16 (2006.01)

(52) U.S. Cl. .................. 536/23.2; 435/320.1; 435/243; 435/254.2; 435/254.23; 536/23.74

(58) Field of Classification Search ..................... None
See application file for complete search history.

(56) References Cited

U.S. PATENT DOCUMENTS

| 4,808,537 | A | 2/1989 | Stroman et al. |
| 5,965,389 | A | 10/1999 | Raymond et al. |
| 2003/0215920 | A1* | 11/2003 | Cregg ........................ 435/69.1 |

OTHER PUBLICATIONS

Guo HH, Choe J, Loeb LA, Protein tolerance to random amino acid change, 2004, Proc Natl Acad Sci USA, 101: 9205-9210.*
Houard S, Heinderyckx M, Bollen A, Engineering of non-conventional yeasts for efficient synthesis of macromolecules: the methylotrophic genera, 2002 Biochimie 84: 1089-1093.*
Kennel, D.E., "Principles and Practices of Nucleic aci Hybridization", 1971, Progr. Nucl. Acid. Res. Mol. Biol., vol. 11: pp. 259-301.*
Van Den Berg, et al. (1996) "Expression cassettes for formaldehyde and fluoroacetate resistance, two dominant markers in *Saccharomyces cerevisiae.*" YEAST, vol. 13, 551-559, pp. 551-559.
Fernandez, et al. (1997) "Formaldehyde dehydrogenase from yeast and plant." *Advances in Experimental Medicine and Biology*, vol. 414, pp. 373-381.
Grey, et al. (1996) "Overexpression of ADH1 confers hyper-resistance to formaldehyde in *Saccharomyces cerevisiae.*" *Current Genetics*, vol. 29, pp. 437-440.
Hur, et al. (1992) "Cloning and characterization of the ADH5 gene encoding human alcohol dehydrogenase 5, formaldehyde dehydrogenase." *Gene*, vol. 121, pp. 305-311.
H. R. Johnson, et al. (1996) "Positive selection for peroxisome-deficient mutants of the methylotrophic yeast *Pichia pastoris.*" XP-002125606, 497a.
M.A. Johnson, et al. (1996) "Positive selection for peroxisome-deficient mutants of the methylotrophic yeast *Pichia pastoris.*" *Molecular Biology of the Cell*, Annual Meeting of the 6th International Congress on Cell Biology and the 36th American Society for Cell Biology, vol. 7, No. Suppl, 7-11 Dec. 1996, p. 497A, San Francisco, California, USA.
Giri, et al. (1989) "Cloning and comparative mapping of a human class III (X) alcohol dehydrogenase cDNA." *Biochemical and Biophysical Research Communications*, vol. 164, No. 1, pp. 453-460, Sep. 1, 2005.
Sasnauskas et al. (1992) "Cloning and analysis of a *Candida maltosa* gene which confers resistance to formaldehyde in *Saccharomyces cerevisiae.*" *Gene*, NL. Elsevier Biomedical Press., Amsterdam, vol. 122, No. 122, p. 207-211-211.
Shen, et al. (1998) "A strong nitrogen source-regulated promoter for controlled expression of foreign genes in the yeast *Pichia pastoris.*" *Gene*, vol. 216, No. 1, pp. 93-102.
Stasyk, et al. (1996) "Mutants of the methylotrophic yeast *Hansenula polymorpha* with impaired catabolite repression." *Microbiology*, vol. 66, No. 6, pp. 755-750.
Tschopp, et al. (1987) "Expression of the lacZ gene from two methanol-regulated promoters in *Pichia pastoris.*" *Nucleic Acids Research*, vol. 15, No. 9, pp. 3859-3876.
Uotila, et al. (1989) "Glutathione-dependent oxidoreductases: formaldehyde dehydrogenase." *Coenzymes Cofactors*, vol. 3, pp. 517-51.
Wehner, et al. (1992) "Molecular structure and genetic regulation of SFA, a gene responsible for resistance to formaldehyde in *Saccharomyces cerevisiae*, and characterization of its protein product." *Molecular and General Genetics*, vol. 237, pp. 351-358.

* cited by examiner

*Primary Examiner*—Scott D. Priebe
*Assistant Examiner*—Michael Burkhart
(74) *Attorney, Agent, or Firm*—Scully, Scott, Murphy & Presser, P.C.

(57) ABSTRACT

The present invention provides formaldehyde dehydrogenase genes (FLD) from methylotrophic yeasts. The FLD structural genes confer resistance to formaldehyde and are therefore useful as a selectable marker in methylotrophic yeasts. The FLD promoter sequences are strongly and independently induced by either methanol as sole carbon source (with ammonium sulfate as nitrogen source) or methylamine as sole nitrogen source (with glucose as carbon source). Induction under either methanol, methylamine or both provides levels of heterologous gene expression comparable to those obtained with the commonly used alcohol oxidase I gene promoter ($P_{AOX1}$). The FLD promoter of *Pichia pastoris* ($P_{FLD1}$) is an attractive alternative to $P_{AOX1}$ for expression of foreign genes in *P. pastoris*, allowing regulation by carbon (methanol) or nitrogen (methylamine) source within the same expression strain. Yeast strains, expression cassettes, expression vectors, and host cells comprising an FLD gene promoter and 3' termination sequence are also provided.

4 Claims, 12 Drawing Sheets

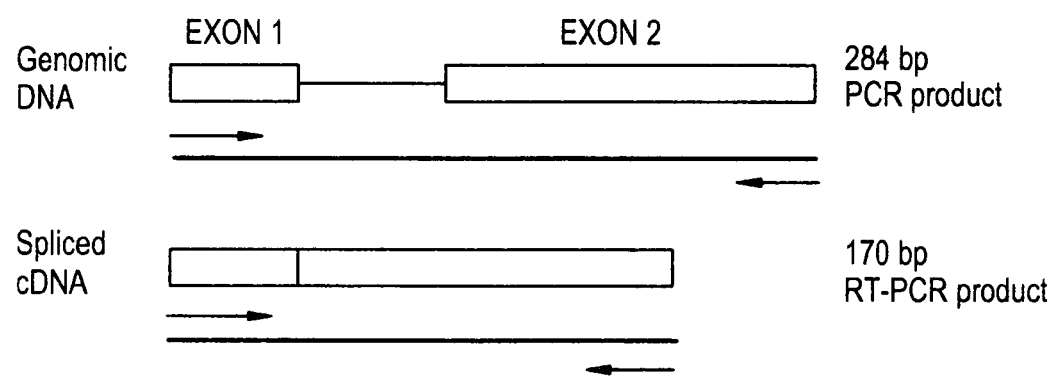

```
661  GGT GCT GCT ATC AAC ACT GCT AAG TCT AAG GGT GAC AAG ATC GGT GTG TTT GGT GCT
183   G   A   A   I   N   T   A   K   S   K   G   D   K   I   G   V   F   G   A
721  GGA TGT ATT GGA TTA TCT GTC ATC CAA GGT GCA TGG ATC GCA AGC GAG ACT AAG ATT
203   G   C   I   G   L   S   V   I   Q   G   A   W   I   A   S   E   T   K   I
781  GTA ATT GAC ATC AAT GAT TCA AAG GCG CAA TGG AAA GCA TTT GGT GCA ACT ATC TTT
223   V   I   D   I   N   D   S   K   A   Q   W   K   A   F   G   A   T   I   F
841  GTC AAT CCT ACA ACC TTA CCA GAA GGT TAC ATT GAC GTT ATT GAT TAC CTT GAT ACT
243   V   N   P   T   T   L   P   E   G   Y   I   D   V   I   D   Y   L   D   T
901  GAC GGA GGC TTT GAC TAT ACC TTC GAC TGT GTT AAT GTT CAA GTA ATG AGA AAT GCA
263   D   G   G   F   D   Y   T   F   D   C   V   N   V   Q   V   M   R   N   A
961  CTT GAA TCT TGC CAC AAG GGT TGG GGT TCG GAG TTG GTC ATC ATC GTC GCT GCT GGT
283   L   E   S   C   H   K   G   W   G   S   E   L   V   I   I   V   A   A   G
1021 AAA GAA ATC TCT ACC CGT CCT CCT CAG TTC ACT GGC AGA GTC TGG AGA GGA TGC GCC
303   K   E   I   S   T   R   P   P   Q   F   T   G   R   V   W   R   G   C   A
1081 TTT GGA GGT ATC AAG GGA CGT ACT CAA ATG CCA TCT TTG GTT CAG GAC TAT CTT GAT GGT
323   F   G   G   I   K   G   R   T   Q   M   P   S   L   V   Q   D   Y   L   D   G
1141 AAG ATT AAA GTT GAC GAG TTT ATC ACA CAT GAC AGA CAT GAC AAC ATC AAC AAA GCA
343   K   I   K   V   D   E   F   I   T   H   D   R   H   D   N   I   N   K   A
1201 TTT CAT GAC ATG CAT GCT GGA AAC TGT CGT GCT GTG ATT ACT ATG CAC TAA gtacgac
363   F   H   D   M   H   A   G   N   C   R   A   V   I   T   M   H   *

1262 gtatgatgaatgagttagtttatgtaaggcccgatctcagctaggacgtttatagaccctatgtatatatgtatgtatac
1342 gtatatacctcaaactcattttatgctagtgaaggattgttgttttcatcgttatgtccgaagatacatcaatacagcgtt
1422 tcttgattgtaccaaacactcccagtagattctccagtctcgctagttaccttcgcgttatgatcgacgctctgtg
1502 aaaaaataaaaaaaaaatgtcaatagtatcgaggttggcttcaaaatcaccagcgttctgtatcggttccgttttgag
1582 cttctacttcctatatccatcatacattcctgctgtgcttgaattcagcagtagaatgtccgatcgatatattgttgca
1662 tatcaacaccacggaaccaactttgaaatagtggtaggggaagtgttctgctaaaccattcaacactcctataacccgctt
1742 tagatcctggaaccaactttgaaatagtggtaggggaagtgttctgctaaaccattcaacactcctataacccgctt
1822 tgtaccagcatgacaactctacagggacaacgcttgtcaagaacgctgttcactcagttgcgctggagagcttagcag
1902 atttattgactcaaactggtcagagaagtatagccctcagttcattcagtcttatatgccttggactttgatcttgaaat
1982 tacccaagagtcgcgtgaaaaatcatctgcattgactacaaacggtatcaagtactttgacttaccaagtactttgaaaagaa
2062 ttctgtagatggtgggcccaaaaatcatctgcattgactacaaacggtaatcacaacatgcttagcttatatggtatctaaact
2142 tgaaacagaagctagtttggttttggacgaggatcc
```

FIG. 5

```
P.pFLD   - MS--TEGQIIKCKAAVAWEAGKDLSIEEIEVLPPRAHEVRVKVEFTGVCH -48
           **    * *  ********* *  ****..  *  **. ****.*.  *****
C.mFLD   - MSESTVGKPITCKAAVAWEAAKPLSIEDVTVAPPKRHEVRIKLYDTGVCH -50

P.pFLD   - TDAYTLSGADAEGSFPVVFGHEGAGVVESVGEGVESVKVGDSVVLLYTPE -98
           ********  *  **.***. ******.***.****  ***** *. *****
C.mFLD   - TDAYTLSGVDPEGAFPVILGHEGAGIVESIGEGVTNVKVGDHVIALYTPE -100

P.pFLD   - CRECKFCLSGKTNLCGKIRATQGKGLLPDGTSRFRCKGKDLFHYMGCSSF -148
           * ***** ****************..*******  ****.. *.****.*
C.mFLD   - CGECKFCKSGKTNLCGKIRATQGKGVMPDGTSRFTCKGKEILHFMGCSTF -150

P.pFLD   - SQYTVVADISVVKVQDEAPKDKTCLLGCGVTTGYGAAINTAKISKGDKIG -198
           ************ ..  *  **.******.*******  **  ***  .
C.mFLD   - SQYTVVADISVVAINPKAEFDKACLLGCGITTGYGAATITANVQKGDNVA -200

P.pFLD   - VFGAGCIGLSVIQGAVSKGASEIIVIDINDSKKAWADQFGATKFVNPTTL -248
           *** * .*******    .**. **..** *  *    *** ***** *
C.mFLD   - VFGGGIVGLSVIQGCAERGAAQIILVDISDKKEEWGQKLGATAFVNPTKL -250

P.pFLD   - PEGTNIVDYLIDITDGGFDYTFDCTGNVQVMRNALESCHKGWGESIIIGV -298
           ****  ***  **..****  *.********.******.****** *.****
C.mFLD   - PEGTTIVDKLIEMTDGGCDFTFDCTGNVGVMRNALEACHKGWGTSVIIGV -300

P.pFLD   - AAAGKEISTRPFQLVTGRVWRGCAFGGIKGRTQMPSLVQDYLDGKIKVDE -348
           ****************  *.*  ****.***.*.*  .*.  *****.**.*
C.mFLD   - AAAGKEISTRPFQLVTGRTWKGAAFGGVKGRSQLPGIVNNYLDGKLKVEE -350

P.pFLD   - FITHRHDLDNINKAFHDMHAGNCIRAVITMH -379
           *****  *  ***** .****  ***** .  .
C.mFLD   - FITHREPLAAINKAFEEMHAGDCIRAVVDLS -381
```

FORMALDEHYDE DEHYDROGENASE GENES FROM METHYLOTROPHIC YEASTS

CROSS REFERENCE TO RELATED APPLICATIONS

The present application is a divisional of Ser. No. 09/345,828, filed Jul. 2, 1999, now U.S. Pat. No. 6,730,499, issued May 4, 2004, which claims the benefit of Provisional Application Ser. No. 60/091,699, filed Jul. 3, 1998.

STATEMENT REGARDING FEDERALLY SPONSORED RESEARCH OR DEVELOPMENT

This work was supported in part from grants from the U.S. National Institutes of Health (DK43698) and the U.S. National Science Foundation (MCB-9514289). The government may have rights in the invention.

BACKGROUND OF THE INVENTION

*Pichia* is a methylotrophic yeast that is widely used for the production of heterologous proteins of industrial and academic interest (Cregg, 1998; Higgins and Cregg, 1998). FLD is an important enzyme in the utilization of methanol as a carbon and energy source (Veenhuis et al., 1983). In methylotrophic yeasts, the methanol metabolic pathway is thought to be nearly the same, beginning with the oxidation of methanol to formaldehyde by alcohol oxidase (AOX), a hydrogen peroxide-producing oxidase that is sequestered in an organelle called the peroxisome. Hydrogen peroxide is then degraded to oxygen and water by catalase, the classic peroxisomal marker enzyme. A portion of the resulting formaldehyde condenses with xylulose-5'-monophosphate in a reaction catalyzed by dihydroxyacetone synthase (DAS), the third peroxisomal methanol pathway enzyme. The products of this reaction, glyceraldehyde-3-phosphate (GAP) and dihydroxyacetone, then leave the peroxisome and enter a cyclic pathway that regenerates xylulose-5'-monophosphate and also generates one net molecule of GAP for every three turns of the cycle. GAP is used for biosynthesis of carbon skeletons for cell growth. Another portion of the formaldehyde leaves the peroxisome and is oxidized to formate by formaldehyde dehydrogenase (FLD) and then to carbon dioxide by formate dehydrogenase (FDH). Both of these reactions produce reducing power in the form of NADH. One model of FLD function is that the NADH generated by FLD and FDH serves as the primary source of energy during growth on methanol (Veenhuis et al., 1983). The second model proposes that most energy for methanol growth comes from the oxidation of one or more of the xylulose-5'-monophosphate cycle intermediates by tricarboxylic acid cycle enzymes, and that the primary role of FLD is to protect the cell from toxic formaldehyde that accumulates with excess methanol in the medium (Sibirny et al., 1990).

In addition to methanol, FLD is also involved in the metabolism of certain methylated amines (e.g. methylamine and choline) as sole nitrogen sources (Zwart et al., 1980). In this pathway, amine groups are first liberated by a peroxisomal amine oxidase, leaving formaldehyde which is further oxidized by FLD and FDH. When growing on methylamine as sole nitrogen source, high levels of FLD are induced even in the presence of excess glucose. Thus, the primary role of FLD in methylamine metabolism appears to be for protecting cells from the toxic effects of formaldehyde and not for generating carbon or energy.

FLD synthesis is regulated independently in response to either methanol as sole carbon source and energy source or to methylamine as sole nitrogen source. Thus, for example, only low levels of FLD are observed in cells growing on glucose- and ammonium ion-containing medium, whereas on either methanol-ammonium ion or glucose-methylamine media, FLD levels are high.

In the *Pichia* system, most foreign genes are expressed under the transcriptional control of the *P. pastoris* alcohol oxidase 1 gene promoter ($P_{AOX1}$), the regulatory characteristics of which are well suited for this purpose. The promoter is tightly repressed during growth of the yeast on most common carbon sources, such as glucose, glycerol, or ethanol, but is highly induced during growth on methanol (Tschopp et al., 1987; U.S. Pat. No. 4,855,231 to Stroman, D. W., et al). For production of foreign proteins, $P_{AOX1}$-controlled expression strains are initially grown on a repressing carbon source to generate biomass and then shifted to methanol as the sole carbon and energy source to induce expression of the foreign gene. One advantage of the $P_{AOX1}$ regulatory system is that *P. pastoris* strains transformed with foreign genes whose expression products are toxic to the cells can be maintained by growing under repressing conditions.

Although many proteins have been successfully produced using $P_{AOX1}$, this promoter is not appropriate or convenient in all settings. For example, in shake-flask cultures, methanol rapidly evaporates, and it is inconvenient to monitor methanol concentrations and repeatedly add the compound to the medium. In addition, the storage of large amounts of methanol needed for the growth and induction of $P_{AOX1}$-controlled expression strains in large-volume high-density fermentor cultures is a potential fire hazard. There is a need therefore, for an alternative promoter to $P_{AOX1}$, which is both transcriptionally efficient and regulatable by a less volatile and flammable inducer. The present invention provides the *P. pastoris* and *Hansenula polymorpha* formaldehyde dehydrogenase gene (FLD) promoter having both properties.

In addition, there is a need for a selectable marker which functions in methylotrophic yeasts other than a selectable marker which is an antibiotic resistance gene. At present, only the $Zeo^R$ gene can be used to transform into *P. pastoris* strains independent of their genotype. In addition, $Zeo^R$ is the only that gene can be used to directly select for *P. pastoris* strains that receive multiple copies of an expression vector (by increasing the concentration of Zeocin in selective medium). A second gene which confers resistance to the antibiotic G418 ($G418^R$) can be used to screen for multicopy expression strains of *P. pastoris* but its use requires that an auxotrophic/biosynthetic gene selection marker must also be included in vectors to select for transformants. The FLD structural gene of the present invention may be used as a selectable marker in methylotrophic yeast cells and does not confer resistance to antibiotics.

SUMMARY OF THE INVENTION

The present invention is directed to isolated nucleic acid sequences comprising a formaldehyde dehydrogenase gene (FLD) from methylotrophic yeasts. In one embodiment of the invention, the isolated nucleic acids comprise sequences which hybridize under low stringency conditions to at least one of the nucleotide sequences set forth in SEQ ID NO:1, SEQ ID NO:5, or a sequence complementary to the sequence set forth in SEQ ID NOs: 1 or 5.

Also provided is an FLD gene from *Pichia pastoris* (FLD1) having the restriction map set forth in FIG. 7 and an FLD gene from *Hansenula polymorpha* having the restriction map shown in the cross hatched area of FIG. 10.

In one embodiment of the invention, there is provided an isolated nucleic acid comprising an FLD gene from a methylotrophic yeast with a coding sequence having a sequence homology of about 70% to about 85% when compared to the nucleotide sequence set forth in SEQ ID NO:5. In another embodiment of the invention, there is provided an isolated nucleic acid comprising an FLD gene from a methylotrophic yeast with a coding sequence having a sequence homology of about 85% to about 95% when compared to the nucleotide sequence set forth in SEQ ID NO:5. In still another embodiment, there is provided an isolated nucleic acid comprising an FLD gene from a methylotrophic yeast with a coding sequence having a sequence homology of greater than about 95% when compared to the nucleotide sequence set forth in SEQ ID NO:5. Isolated nucleic acids comprising the sequences set forth in SEQ ID NO:1 or SEQ ID NO:5 are also provided.

The present invention also provides an isolated nucleic acid from a methylotrophic yeast comprising an FLD promoter. The promoter is located upstream from the translational start codon of an FLD gene having a coding sequence with a sequence homology of about 70% to about 85% when compared to the nucleotide sequence of the FLD coding sequence set forth in SEQ ID NO:5. In another embodiment, there is provided an isolated nucleic acid from a methylotrophic yeast comprising an FLD promoter from an FLD gene having a coding sequence with a sequence homology of about 85% to about 95% when compared to the nucleotide sequence of the FLD coding sequence set forth in SEQ ID NO:5. In a preferred embodiment, the promoter is from an FLD gene having a coding sequence with a sequence homology of greater than about 95% when compared to the nucleotide sequence of the FLD coding sequence set forth in SEQ ID NO:5. Particularly exemplified is a *Pichia pastoris* FLD1 promoter comprising the sequence set forth in SEQ ID NO:3.

Also in accordance with the present invention; there is provided an isolated nucleic acid comprising an FLD 3' termination sequence from a methylotrophic yeast. The 3' termination sequence is located downstream from the translational stop codon of an FLD gene having a coding sequence with a sequence homology of at about 70% to about 85% when compared to the nucleotide sequence of the FLD coding sequence set forth in SEQ ID NO:5. In another embodiment of the invention, there is provided an isolated nucleic acid comprising an FLD 3' termination sequence from a gene having a coding sequence with a sequence homology of at about 85% to about 95% when compared to the nucleotide sequence of the FLD-coding sequence set forth in SEQ ID NO:5. In a preferred embodiment of the invention, there is provided an isolated nucleic acid comprising an FLD 3' termination sequence from a gene having a coding sequence with a sequence homology of greater than about 95% when compared to the sequence set forth in SEQ ID NO:5.

Also provided are isolated nucleic acids comprising an FLD gene wherein said FLD gene encodes a product having an amino acid sequence identity of about 30% to about 49%, or about 50% to about 90%, or greater than about 90% when compared to the amino acid sequence as set forth in SEQ ID NO:2.

In addition, the present invention also provides an isolated nucleic acid comprising at least one of a promoter, coding sequence or 3' termination sequence from an FLD gene wherein said FLD gene encodes a product having an amino acid sequence identity of about 30% to about 49%, or about 50% to about 90%, or greater than about 90% when compared to the amino acid sequence as set forth in SEQ ID NO:2.

In addition, the present invention provides expression cassettes, vectors and host cells comprising the subject isolated nucleic acids.

Also in accordance with the present invention, there is provided a method for directing expression of a heterologous gene in a methylotrophic yeast. The method comprises introducing into a methylotrophic yeast cell an isolated nucleic acid comprising an FLD promoter isolated from a methylotrophic yeast, said promoter operably linked at its 3' end to the 5' end of a heterologous gene, said heterologous gene operably linked at its 3' end to the 5' end of a termination sequence which functions in a methylotrophic yeast. The methylotrophic yeast cells are grown in a medium having a suitable carbon source such as glycerol or glucose and having a suitable nitrogen source such as an ammonium salt or ammonium hydroxide. After the carbon or nitrogen source is depleted, expression of said heterologous gene is induced by addition of methanol or methylamine or both methanol and methylamine. Expression may also be induced by the addition of formaldehyde, formate, or a methylated amine.

A method for selecting a formaldehyde resistant host cell is also provided by the present invention. The method comprises transforming a methylotrophic yeast cell with a vector comprising an FLD gene, said FLD gene operably linked at its 5' end to an FLD promoter or a heterologous promoter which functions in said yeast cell, said FLD gene operably linked on its 3' end to a 3' termination sequence which functions in said yeast cell. Host cells are grown in the presence of formaldehyde and a yeast cell which grows in the presence of formaldehyde is selected.

The present invention also provides a strain of methylotrophic yeast which is defective in an FLD gene (fld) such as *Pichia pastoris* GS241 (fld1-1). Also provided is a strain of methylotrophic yeast which is defective in an FLD gene and auxotrophic for another biosynthetic gene.

In accordance with the present invention, a kit is provided which comprises an expression cassette comprising an FLD promoter and a 3' termination sequence which functions in a methylotrophic yeast. At least one restriction site is located between the FLD promoter and 3' termination sequence so that a heterologous gene may be inserted and operably linked to the promoter and the 3' termination sequence. Also included in the kit is a vector which either replicates in a methylotrophic yeast or which integrates into the genome of a methylotrophic yeast, which vector comprises a marker gene and one or more restriction sites for insertion of the expression cassette.

In addition, the present invention provides a kit which comprises an expression vector comprising an FLD gene as a selectable marker gene and an expression cassette. The expression cassette comprises a promoter and a 3' termination sequence which functions in a methylotrophic yeast, and has at least one restriction site located between the promoter and 3' termination sequence so that a heterologous gene may be inserted and operably linked to the promoter and said 3' termination sequence.

BRIEF DESCRIPTION OF THE DRAWINGS

FIG. 3A shows exon analysis of the FLD1 gene. A diagram of the expected products from PCR of unspliced (genomic) and spliced (cDNA) DNAs is indicated. Locations of the hybridized primers used in the PCR reactions are shown as convergent arrows.

FIGS. 4A–4B are the nucleotide (SEQ ID NO:1) and deduced amino acid (SEQ ID NO:2) sequences of *P. pastoris* FLD1 gene and its product.

FIG. 5 is a comparison of the predicted amino acid sequences of *P. pastoris* (SEQ ID NO:2) and *C. maltosa* (SEQ ID NO:6) FLD proteins. Sequences were aligned using PC gene software. The character "*" between sequences indicates residues that are identical. The character "." indicates similar residues. Similar residues are defined as: A,S,T; D,E; N,Q; R,K; I,L,M,V; F,Y,W.

DETAILED DESCRIPTION OF THE INVENTION

The present invention is directed to isolated nucleic acid sequences comprising formaldehyde dehydrogenase genes (FLD) from methylotrophic yeasts. The product of the FLD gene, formaldehyde dehydrogenase, confers resistance to formaldehyde. In one aspect of the invention, an FLD coding sequence may be used with its own 5' and 3' regulatory region or with a heterologous 5' and 3' regulatory region in order to function as a selectable marker in a methylotrophic yeast cell. The subject FLD coding sequences are therefore advantageous when use of antibiotic resistance genes as selectable markers is to be avoided.

In accordance with the present invention, a subject FLD gene can be used as a selectable marker that, like $Zeo^R$, can be selected for independent of the genotype of the *P. pastoris* strain and, like $Zeo^R$ and $G418^R$, can be used to directly select strains that receive multiple copies of an expression vector. However, unlike $Zeo^R$ and $G418^R$, the *P. pastoris* FLD1 gene is native to *P. pastoris* and does not confer resistance to an antibiotic.

Figure 7:
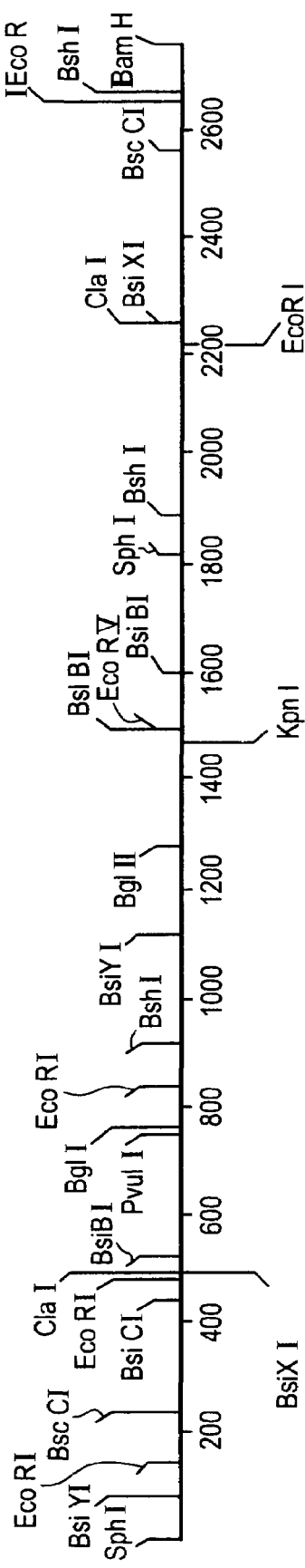
FIG. 7 is a restriction map of the *Pichia pastoris* FLD1 gene.
Figure 10:
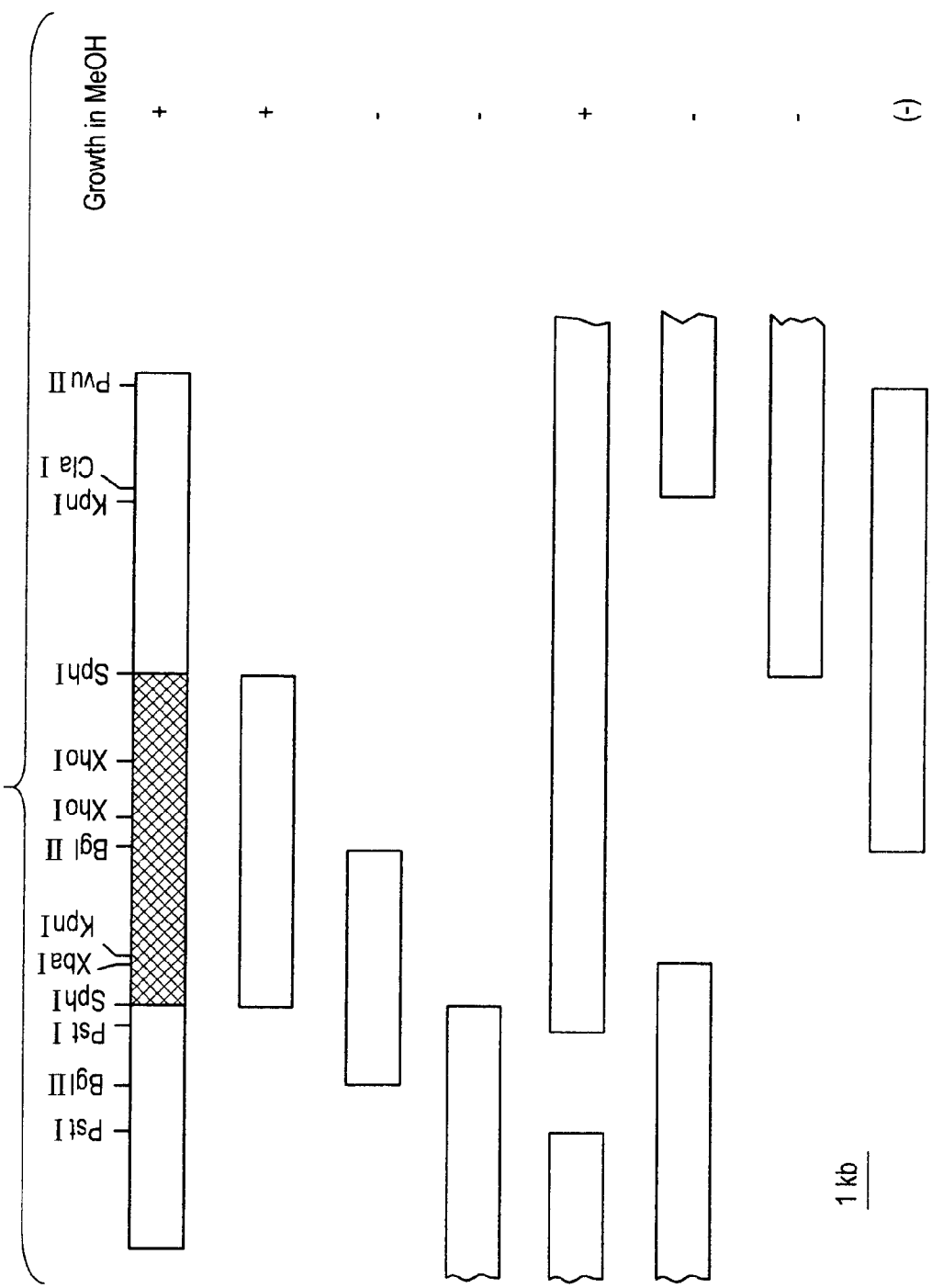
FIG. 10 is a restriction map of an *H. polymorpha* DNA fragment containing the FLD gene.

In one aspect of the present invention, there are provided FLD genes from *Pichia pastoris* and *Hansenula polymorpha* having the restriction maps set forth in FIG. 7 and the cross hatched region of FIG. 10, respectively. FLD expression in response to methanol or methylamine is controlled at the transcriptional level. The FLD gene from *Pichia pastoris* (FLD1) can be further described in terms of its nucleotide sequence which sequence is set forth in FIGS. 4A–4B (SEQ ID NO:1). The nucleotide sequence of the coding region of the FLD1 gene is set forth in SEQ ID NO:5.

In another aspect of the invention, there are provided inducible 5' regulatory regions from FLD genes (used herein interchangeably with "FLD promoters"), isolated from methylotrophic yeasts which 5' regulatory regions are useful for efficient expression of heterologous genes in cells of a methylotrophic yeast. The subject FLD 5' regulatory regions are strongly and independently induced by different carbon and/or energy sources such as methanol, formaldehyde, and formate. Neither formaldehyde nor formate are carbon sources in a true sense since *Pichia pastoris* does not utilize carbon from such compounds, but only obtains energy from their oxidation. The subject FLD 5' regulatory regions are also strongly and independently induced by different nitrogen sources such as methylamine, choline, and other methylated amines. Thus for example, the *Pichia pastoris* FLD1 promoter is strongly and independently induced by either methanol as sole carbon source (with ammonium hydroxide or an ammonium salt as nitrogen source) or methylamine as sole nitrogen source (with a carbon sugar as carbon source). Examples of non-inducing nitrogen sources include ammonium sulfate, ammonium nitrate, ammonium chloride and ammonium hydroxide. Examples of non-inducing carbon sources include glycerol and glucose.

Figure 8:
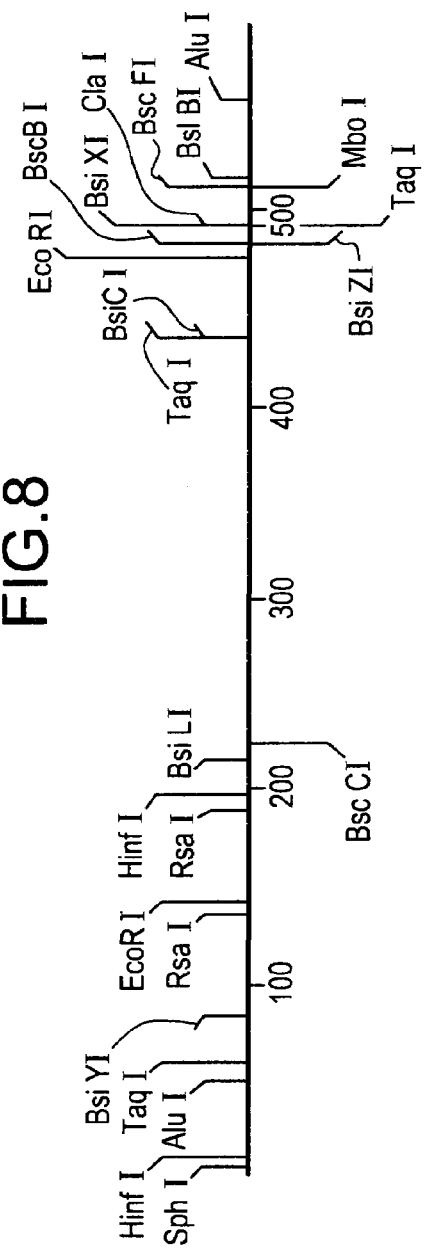
FIG. 8 is a restriction map of $P_{FLD1}$.

Accordingly, the present invention provides an isolated nucleic acid molecule comprising about 600 base pairs or more of nucleotide sequence located upstream from the translational start codon of an FLD gene from a methylotrophic yeast. Particularly exemplified is the promoter from the *Pichia pastoris* FLD gene (FLD1) having the restriction map illustrated in FIG. 8. In a preferred embodiment, the FLD1 gene promoter has the nucleotide sequence as set forth as SEQ ID NO:3. Also exemplified is the FLD promoter from *Hansenula polymorpha* having the restriction sites indicated in the cross hatched portion of FIG. 10.

The present invention also provides FLD 3' termination sequences from methylotrophic yeasts. Accordingly, the present invention provides an isolated nucleic acid comprising about 300 nucleotides or more of sequence located downstream from the translational stop codon of an FLD gene. For example, the 3' termination sequence may comprise nucleotides 1255–1555 of FIG. 4 (SEQ ID NO:4). In another embodiment of the invention, the 3' termination sequence is from the *Hansenula polymorpha* FLD gene which gene is shown as the cross hatched area in FIG. 10.

Modifications to the FLD1 promoter as set forth in SEQ ID NO:3, which maintain the characteristic property of promoting expression by either methanol, formaldehyde, or formate induction or by methylamine choline or other methylated amine induction, are within the scope of the present invention. Modifications to the 3' termination sequence as set forth in SEQ ID NO:4, which maintain the characteristic property of stabilizing mRNA transcription products of a gene are also within the scope of the present invention. Similarly, modifications to the *Pichia pastoris*

FLD1 coding sequence (FIG. 4, SEQ ID NO:5) which maintain the characteristic property of coding for a biologically active formaldehyde dehydrogenase are within the scope of the present invention. Such modifications include insertions, deletions and substitutions of one or more nucleotides.

The present invention also provides methylotrophic yeast strains which are defective in the FLD gene, i.e., fld mutants. Such strains may be generated by exposing methylotrophic yeast cells to a mutagen such as nitrosoguanidine and screening for strains unable to utilize methanol as sole carbon source and methylamine as sole nitrogen source. Complementation and other genetic techniques may then be used to confirm that a methylotrophic yeast strain is an fld mutant. In accordance with the present invention, a *Pichia pastoris* fld strain is provided and designated GS241 (fld1-1). An fld mutant methylotrophic yeast strain may be crossed to another strain which is an auxotrophic mutant for a biosynthetic gene or which has a different selectable marker. For example, the present invention provides a *Pichia pastoris* yeast strain which is methanol-utilization defective (Mut⁻) and auxotrophic for histidine (His⁻), designated MS105 (fld1-1 his4).

An FLD gene may be isolated from a methylotrophic yeast using classic functional complementation techniques. Briefly stated, a genomic library of DNA from a methylotrophic yeast is cloned into a vector which replicates in a methylotrophic yeast. The vectors are used to transform a methylotrophic yeast which is an fld mutant. Cells which grow in the presence of methanol (or any of the above-described inducing agents) are selected as having a functional FLD gene from the genomic library. The vector is isolated from the complemented yeast cells and restriction mapped. Fragments of the vector insert may be subcloned and used to transform an fld mutant and a smaller fragment which still complements the fld mutant isolated. The insert of this vector may be sequenced and the FLD gene open reading frame (ORF) identified. As described in Examples 2 and 3, both the *Pichia pastoris* FLD1 gene and the *Hansenula polymorpha* FLD gene were isolated by functional complementation.

Nucleic acid molecules corresponding to coding sequences, promoters or 3' termination sequences of an FLD gene of a methylotrophic yeast may also be obtained by using the entire FLD1 gene, the entire coding sequence of the FLD1 gene, or portions of the FLD1 coding sequence (including fragments and oligonucleotides) as a probe and hybridizing with a nucleic acid molecule(s) from a methylotrophic yeast. Nucleic acid molecules hybridizing to the *Pichia pastoris* entire FLD gene, (SEQ ID NO:1), or to the FLD coding sequence (FIG. 4, SEQ ID NO:5) or portion of the nucleotide sequence set forth in SEQ ID NO:5, can be isolated, e.g., from genomic libraries by techniques well known in the art. Methods considered useful in obtaining genomic DNA sequences corresponding to the *Pichia pastoris* FLD gene of the present invention by screening a genomic library are provided in Sambrook et al. (1989), *Molecular Cloning: A Laboratory Manual*, Cold Spring Harbor, N.Y., for example, or any of the myriad of laboratory manuals on recombinant DNA technology that are widely available.

A subject FLD gene can be derived from restriction endonuclease digestion of isolated FLD genomic clones. Thus, for example, the known nucleotide or amino acid sequence of the *Pichia pastoris* FLD1 gene (FIG. 4, SEQ ID NOs:1 and 2) is aligned to the nucleic acid or deduced amino acid sequence of an isolated putative FLD genomic clone and the 5' regulatory sequence (i.e., sequence upstream from the translational start codon of the coding region), coding sequence, and 3' regulatory sequence (i.e., sequence downstream from the translational stop codon of the coding region) of the isolated FLD genomic clone located.

A subject FLD promoter, 3' termination sequence or coding sequence may be generated from genomic clones having excess 5' flanking sequence, excess coding, sequence, or excess 3' flanking sequence by e.g., in vitro mutagenesis. In vitro mutagenesis is helpful for introducing convenient restriction sites. There are various commercially available kits particularly suited for this application such as the T7-Gen in vitro Mutagenesis Kit (USB, Cleveland, Ohio) and the QuikChange Site Directed Mutagenesis Kit (Stratagene, San Diego, Calif.). Alternatively, PCR primers can be defined to allow direct amplification of a subject FLD promoter, coding sequence and 3' termination sequence.

Using the same methodologies, the ordinarily skilled artisan can generate one or more deletion fragments of the FLD1 promoter as set forth in SEQ ID NO:3. Any and all deletion fragments which comprise a contiguous portion of the nucleotide sequence set forth in SEQ ID NO:3 and which retain the capacity to promote expression by either methanol, formaldehyde, or formate induction or else which retain the capacity to promote expression by either methylamine, choline or other methylated amine induction are contemplated by the present invention. Similarly, any and all deletion fragments which comprise a contiguous portion of the sequence set forth in SEQ ID Nos:4 and 5 and which retain the capacity to stabilize mRNA transcription products of a gene or retain the capacity to code for a biologically active FLD, respectively, are within the scope of the present invention.

Figure 4A:
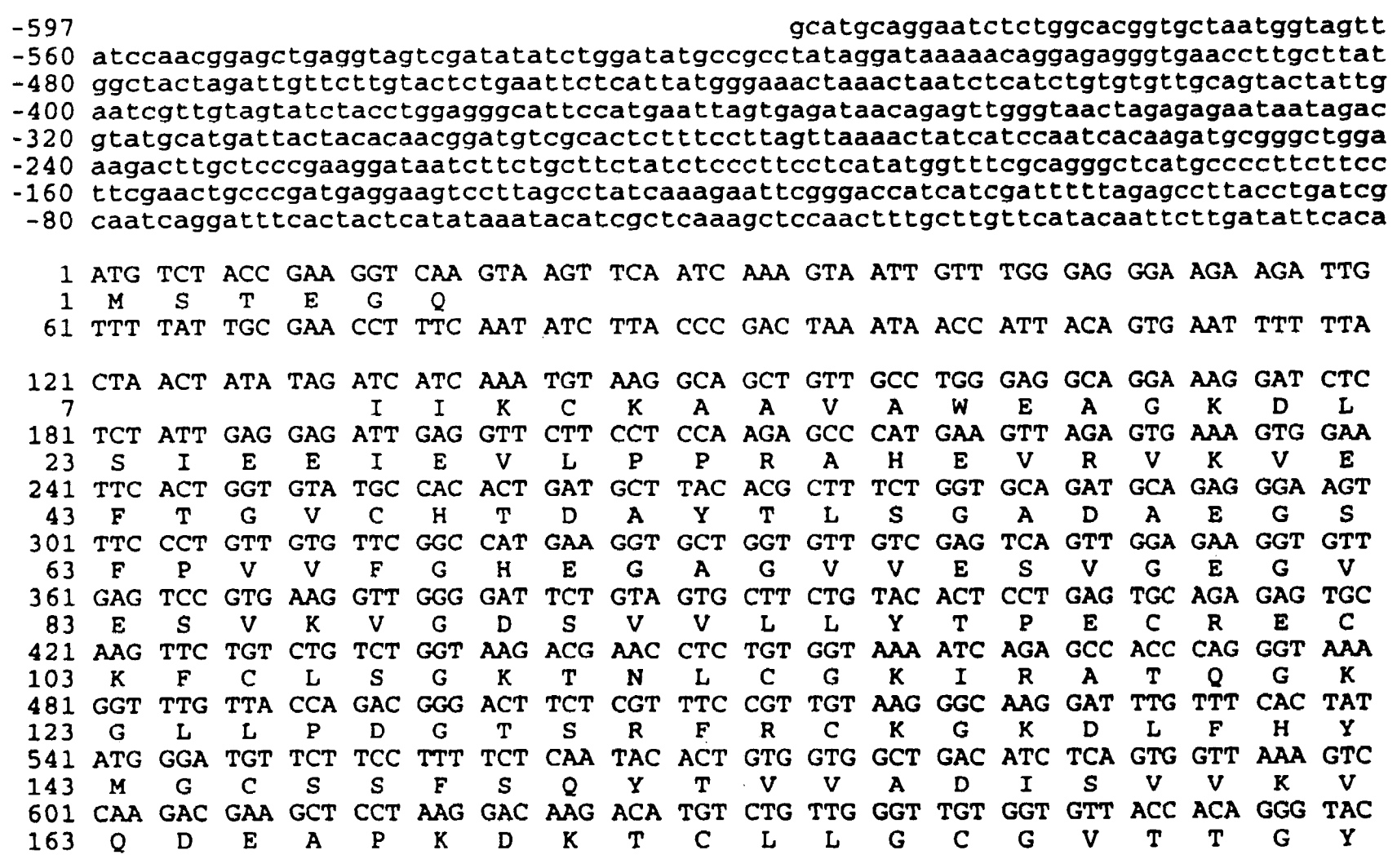

In addition to the *Pichia pastoris* FLD1 promoter which nucleotide sequence is set forth as nucleotides −537 to −1 in FIGS. 4A–4B (SEQ ID NO:3), the present invention is directed to other promoter sequences which correspond to FLD genes in other methylotrophic yeasts. As defined herein, such related sequences which promote expression by methanol, formaldehyde, or formate induction or else which promote expression by either methylamine, choline or other methylated amine induction, may be described in terms of their location upstream from the translational start codon of an FLD coding sequence, which coding sequence is described in terms of percent homology on a nucleotide level to the nucleotide coding sequence as set forth in FIGS. 4A–4B (SEQ ID NO:5).

Alternatively, FLD coding sequences from methylotrophic yeasts may be defined in terms of their ability to hybridize to the exemplified *Pichia pastoris* FLD1 gene (SEQ ID NO:1) or FLD1 coding sequence (SEQ ID NO:5) under low stringency hybridization conditions. The present invention therefore contemplates nucleic acid sequences isolated from a methylotrophic yeast comprising a promoter, coding region or 3' termination sequence corresponding to an FLD gene which coding region of such FLD gene hybridizes under low stringency conditions to the FLD gene nucleic acid sequence as set forth in SEQ ID Nos:1 or 5, or sequences complementary to the sequences set forth in SEQ ID NOS:1 or 5. The promoter, coding region or 3' termination sequences of an FLD gene which coding region hybridizes to a sequence as set forth in SEQ ID NOs:1 or 5, may differ in one or more nucleotide positions in comparison with SEQ ID NOs:1 through 5 as long as such coding sequence from an FLD gene codes for a biologically active FLD, or as long as such FLD promoter is independently induced by either methanol, formaldehyde, or formate as energy source or by methylamine, choline or other methylated amine as sole nitrogen source. In addition, a subject 3' termination sequence may differ in one or more nucleotide positions in comparison to SEQ ID NO:4 as long as such 3' termination sequence retains the capacity to stabilize mRNA transcripts when operably linked to a coding sequence.

By "hybridizing" it is meant that such nucleic acid molecules hybridize under conventional hybridization conditions, such as described by, e.g., Sambrook (Molecular Cloning; A Laboratory Manual, 2nd Edition, Cold Spring Harbor Laboratory Press, Cold Spring Harbor, N.Y. (1989)).

FLD genes (genomic sequences) and FLD coding sequences from methylotrophic yeasts may be identified by hybridization to the coding region or portions thereof of FLD1, (SEQ ID NOs:1 and 5, as well as the complementary sequences to SEQ ID NOS:1 AND 5) using conventional hybridization conditions. Preferably, low hybridization conditions are used such as 30% formamide at 37° C. followed by washing in 1× SSC at room temperature and 1× SSC at 60° C. Putative FLD genes ranging in size from about 2 kb to about 3.5 kb or about 2.5 kb to about 3.5 kb which hybridize to SEQ ID NOs:1 or 5 under low stringency conditions may be further characterized by restriction mapping and sequencing. Using the FLD1 gene in the plasmid pYG1 as a probe and hybridizing under such low stringency conditions, the *H. polymorpha* FLD gene may be identified. See Example 3.

FLD promoters and 3' termination sequences may also be defined by the ability of the corresponding coding sequence of the FLD gene (from which the promoter or 3' termination sequence is derived), to hybridize under low stringency conditions to the coding sequence set forth in FIG. 4 (SEQ ID NOs:1 and 5), as well as the complementary sequences to SEQ ID NOs:1 and 5.

FLD structural genes, promoter fragments and terminator sequences of the present invention may also be described in terms of percent homology on a nucleotide level to the nucleotide sequence provided herein. There are a number of computer programs that compare and align nucleic acid sequences which one skilled in the art may use for purposes of determining sequence homologies. For example, the PC/Gene program may be used (Release 6.6, IntelliGenetics, Inc., Mountainview, Calif.) with an open gap cost of 15 and a unit gap cost of 10.

As used herein, a sequence homology percentage value includes not only the percent homology of an isolated nucleic acid when compared to the single strand sequence set forth in a particular SEQ ID NO., but also includes the percent homology of an isolated nucleic acid when compared to the complementary strand of the single strand sequence set forth in the particular SEQ ID NO., such as SEQ ID NO:5.

Thus, using a computer program such as the PC/Gene program with the parameters set as described above, the subject isolated nucleic acids may be described as follows. In one embodiment of the invention, there is provided an isolated nucleic acid comprising an FLD gene from a methylotrophic yeast which is independently inducible by either methanol as sole carbon source or methylamine as sole nitrogen source and having a coding sequence with a sequence homology of about 70% to about 85% when compared to the nucleotide sequence of the FLD gene as set forth in SEQ ID NO:5. In a preferred embodiment, an isolated nucleic acid comprising an FLD gene which is independently inducible by either methanol as sole carbon source or methylamine as sole nitrogen source has a coding sequence with a sequence homology of about 85% to about 95% when compared to the coding sequence of the FLD gene as set forth in SEQ ID NO:5.

In a most preferred embodiment, an isolated nucleic acid comprising an FLD gene which is independently inducible by either methanol as sole carbon source or methylamine as sole nitrogen source has a coding sequence with a sequence homology of greater than about 95% when compared to the sequence of the FLD coding region as set forth in SEQ ID NO:5.

In another aspect of the present invention, an isolated nucleic acid comprising a promoter from an FLD gene which is independently inducible by either methanol as sole carbon source or methylamine as sole nitrogen source comprises approximately 600 bases pairs or more of nucleotide sequence located upstream (5') from the translation start codon of an FLD gene, whose coding sequence has a sequence homology of about 70% to about 85% when compared to the nucleotide. sequence of the FLD coding sequence as set forth in SEQ ID NO:5. In a preferred embodiment, an isolated nucleic acid comprising a promoter from an FLD gene which is independently inducible by either methanol as sole carbon source or methylamine as sole nitrogen source comprises approximately 600 bases pairs or more of nucleotide sequence located upstream (5')from the translation start codon of an FLD gene, whose coding sequence has a sequence homology of about 85% to about 95% when compared to the nucleotide sequence of the FLD coding sequence as set forth in SEQ ID NO:5.

In a more preferred embodiment, an isolated nucleic acid comprising a promoter from an FLD gene which is independently inducible by either methanol as sole carbon source or methylamine as sole nitrogen source comprises approximately 600 bases pairs or more of nucleotide sequence located upstream (5') from the translation start codon of an FLD gene, whose coding sequence has a sequence homology of greater than about 95% when compared to the nucleotide sequence of the FLD coding sequence as set forth in SEQ ID NO:5. With respect to any of the above-described promoters, preferably, a promoter comprises approximately 600 base pairs or more of nucleotide sequence located immediately upstream (5') to the translational start codon of an FLD gene.

In another aspect of the invention, an isolated nucleic acid comprising an FLD 3' termination sequence from a methylotrophic yeast comprises approximately 300 base pairs or more of nucleotide sequence located downstream (3') from the translational stop codon of an FLD gene, whose coding sequence has a sequence homology of about 70% to about, 85% when compared to the nucleotide sequence of the FLD coding sequence as set forth in SEQ ID NO:5. In a preferred embodiment, an isolated nucleic acid comprising an FLD 3' termination sequence from a methylotrophic yeast comprises approximately 300 base pairs or more of nucleotide sequence downstream (3') from the translational stop codon of an FLD gene, whose coding sequence has a sequence homology of about 85% to about 95% when compared to the nucleotide sequence of the FLD coding sequence as set forth in SEQ ID NO:5. In a most preferred embodiment, an isolated nucleic acid comprising an FLD 3' termination sequence from a methylotrophic yeast comprises approximately 300 base pairs or more of nucleotide sequence located downstream (3') from the translational stop codon of an FLD gene, whose coding sequence has a sequence homology of greater than about 95% when compared to the nucleotide sequence of the FLD coding sequence as set forth in SEQ ID NO:5. With respect to any of the above-described 3' termination sequences, preferably a 3' termination sequence comprises approximately 300 base pairs or more of nucleotide sequence located immediately downstream (3') to the translational stop codon of an FLD gene.

In addition to the aforementioned nucleic acid sequences, the present invention contemplates isolated nucleic acids comprising promoters, coding sequences and 3' termination sequences from an FLD gene whose product has an amino acid sequence identity of about 30% to about 49% when compared to the amino acid sequence set forth in FIGS. 4A–4B (SEQ ID NO:2). In a preferred embodiment, an isolated nucleic acid comprising a promoter, coding sequence or 3' termination sequence from an FLD gene is from an FLD gene whose product has an amino acid sequence identity of about 50% to about 90% when compared to the amino acid sequence set forth in FIG. 4 (SEQ ID NO:2). In a more preferred embodiment, an isolated nucleic acid comprising a promoter, coding sequence or 3' termination sequence from an FLD gene is from an FLD gene whose product has an amino acid sequence identity of greater than about 90% when compared to the amino acid sequence set forth in FIG. 4 (SEQ ID NO:2). In a most preferred embodiment, an isolated nucleic acid comprising a promoter, coding sequence or 3' termination sequence from an FLD gene is from an FLD gene whose product has an amino acid sequence as set forth in FIGS. 4A–4B (SEQ ID NO:2).

In accordance with the present invention, an entire FLD gene (i.e., a genomic sequence comprising FLD coding sequence operably linked to the native FLD promoter and native 3' termination sequence) may also be described by the sequence identity of the product of the coding region. Thus, in one embodiment of the invention, there is provided an FLD gene wherein the amino acid sequence of the product of the FLD gene has a sequence identity of about 30% to about 49% when compared to the amino acid sequence set forth in FIGS. 4A–4B (SEQ ID NO:2). In a preferred embodiment, there is provided an FLD gene wherein the amino acid sequence of the product of the FLD gene has a sequence identity of about 50% to about 90% when compared to the amino acid sequence set forth in FIGS. 4A–4B (SEQ ID NO:2). In a more preferred embodiment, an isolated nucleic acid comprising an FLD gene codes for a product having an amino acid sequence with a sequence identity of greater than about 90% when compared to the amino acid sequence set forth in FIGS. 4A–4B (SEQ ID NO:2). In a most preferred embodiment, an FLD gene codes for a product having an amino acid sequence as set forth in FIGS. 4A–4B (SEQ ID NO:2).

For purposes of determining the degree of sequence identity between a putative FLD amino acid sequence from a methylotrophic yeast and the FLD amino acid sequence provided herewith as SEQ ID NO:2, the BLAST 2.0 program (GenBank, National Center for Biotechnology Information) may be used with all parameters set to default parameters.

To determine the nucleotide sequence of an isolated FLD nucleic acid molecule, any of the various well known techniques may be used. For example, restriction fragments containing an FLD gene from *Pichia pastoris* or other methylotrophic yeast can be subcloned into the polylinker site of a vector such as pBluescript (Stratagene). These pBluescript subclones can then be sequenced by the double-stranded dideoxy method (Chen et al. (1985) *DNA*, 4; 165).

5' regulatory sequence, coding sequence, and 3' termination sequence from a methylotrophic yeast FLD gene which correspond to *Pichia pastoris* FLD gene sequences may also be isolated by applying a nucleic acid amplification technique such as the polymerase chain reaction (PCR) using as primers oligonucleotides derived from sequences set forth in SEQ ID NOs:1, 3, 4, and 5.

Confirmation of independent inducibility of an FLD promoter (including modifications or deletion fragments thereof) from a methylotrophic yeast, can be accomplished by construction of transcriptional and/or translational fusions of specific sequences with the coding sequences of a heterologous gene, transfer of the chimeric gene into an appropriate host, and detection of the expression of the heterologous gene. The assay used to detect expression depends upon the nature of the heterologous sequence. For example, reporter genes, exemplified by β-lactamase (β-lac), β-galactosidase (β-gal), luciferase and chloramphenicol acetyltransferase (CAT) are commonly used to assess transcriptional and translational competence of chimeric constructions. Standard assays are available to sensitively detect the reporter enzyme in a transformed host cell.

An FLD promoter, 3' termination sequence and isolated fragments thereof, are useful in the construction of expression cassettes (also termed herein "chimeric genes") and expression vectors for the expression of heterologous proteins in a methylotrophic host cell. As used herein, "heterologous protein" or "heterologous polypeptide" refers to any protein or polypeptide other than formaldehyde dehydrogenase. As used herein, "heterologous gene" means a gene other than FLD.

As used herein, the term "cassette" refers to a nucleotide sequence capable of expressing a particular gene if said gene is inserted so as to be operably linked to one or more regulatory sequences present in the nucleotide sequence. Thus, for example, the expression cassette may comprise a heterologous gene which is desired to be expressed through methanol or methylamine induction. The expression cassettes and expression vectors of the present invention are therefore useful for promoting expression of any number of heterologous genes upon methanol or methylamine induction.

Some examples of heterologous genes for expression of foreign proteins under control of the subject FLD promoter and for use in the expression cassettes and vectors of the present invention include human serum albumin, invertase, bovine lysozyme, human EGF, mouse EGF, aprotinin, Kunitz protease inhibitor, Hepatitis B surface antigen, tumor necrosis factor, tetanus toxin fragment C, pertussis antigen P69, streptokinase, β-galactosidase, and *Bacillus* sp. crystal protein toxin. For a list of other useful proteins which may be expressed in *Pichia pastoris*, see Higgins, D. R. and Cregg, J. M. (1998) *Methods in Molecular Biology: Pichia Protocols*. Humana Press, Totowa, N.J., Chapter 17, pp. 249–261. Any and all coding sequences are contemplated as heterologous genes for use in the expression cassettes and expression vectors of the present invention.

The expression cassettes of the present invention comprise in the 5' to 3' direction an FLD promoter operably linked a nucleotide sequence coding for a heterologous gene. In a preferred embodiment, the coding sequence for a heterologous gene is further operably linked at its 3' end to a 3' termination sequence. If desired, additional regulatory elements from genes other than FLD or parts of such elements sufficient to cause expression resulting in production of an effective amount of the polypeptide encoded by the heterologous gene are included in the chimeric constructs. For example, signal sequences coding for transit peptides may be used when secretion of a product of a heterologous gene is desired. Such sequences are widely known, readily available and include *Saccharomyces cer-* evisiae alpha mating factor pre pro (αmf), *Pichia pastoris* acid phosphatase (PHO1) signal sequence and the native signal sequence from the protein encoding heterologous gene.

The expression cassette may be inserted into a microorganism host via a vector such as a circular plasmid or linear site-specific integrative vector. The term "operably linked" refers to a juxtaposition wherein the FLD promoter, structural gene, and 3' termination sequence are linked and configured so as to perform their normal function. 3' termination sequences are sequences 3' to the stop codon of a structural gene which function to stabilize the mRNA transcription product of the gene to which the sequence is operably linked, such as sequences which elicit polyadenylation. 3' termination sequences may be obtained from *Pichia* or *Hansenula polymorpha* or other methylotrophic yeast. Examples of *Pichia pastoris* 3' termination sequences useful for the practice of the present invention include termination sequences from the AOX1 gene, p40 gene, HIS4 gene and FLD1 gene.

In accordance with the present invention, the *Pichia pastoris* FLD1 gene, the *Hansenula polymorpha* FLD gene, and other FLD genes isolated from methylotrophic yeasts, may be used as selectable markers in host cells. Either the entire FLD gene, including the native 5' and 3' regulatory sequences or the FLD coding region operably linked to 5' and 3' regulatory regions other than that of an FLD gene may be used.

The isolated nucleic acids comprising an FLD promoter, FLD coding sequence and/or FLD 3' termination sequence, the subject expression cassettes comprising such isolated nucleic acids as well as an entire FLD gene (genomic sequence) or FLD coding sequence operably linked to 5' and 3' regulatory regions other than that of an FLD gene, may be inserted into a vector such as a plasmid. The vector preferably contains a selectable marker gene which functions in a methylotrophic yeast. The selectable marker may be any gene which confers a selectable phenotype upon a methylotrophic yeast and allows such yeast to be identified and selected from untransformed cells. The selectable marker system may include an auxotrophic mutant *Pichia pastoris* host strain and a wild type gene which complements the host's defect. Examples of such systems include the *Saccharomyces cerevisiae* or *Pichia pastoris* HIS4 gene which may be used to complement his4 Pichia strains, or the *S. cerevisiae* or *Pichia pastoris* ARG4 gene which may be used to complement *Pichia pastoris* arg mutants. Other selectable marker genes which function in *Pichia pastoris* include the $Zeo^R$ gene, the $G418^R$ gene, and of course, the FLD genes of the present invention.

The vectors of the present invention may also contain selectable marker genes which function in bacteria. The added bacterial selectable marker permits amplification of the vector in bacterial host cells. Examples of bacterial selectable marker genes include ampicillin resistance ($Amp^r$), tetracycline resistance ($Tet^r$) neomycin resistance, hygromycin resistance, and zeocin resistance ($Zeo^R$).

In addition, the vectors of the present invention may include sequences responsible for replication and extrachromosomal maintenance in bacteria such as *E. coli*. The use of such sequences allows for amplification of the vector in bacteria and thus production of large amounts of the vector DNA. Examples of bacterial origins of replication include colisin, col D1, col E1 and others known to skilled artisans.

The vectors of the present invention may also contain an autonomous replication sequence (ARS) such as described in U.S. Pat. No. 4,837,148, issued Jun. 6, 1989 to James M. Cregg. The disclosure of U.S. Pat. No. 4,837,148 is incorporated herein as if fully set forth. The autonomous replication sequences disclosed by Cregg provide a suitable means for maintaining plasmids in *Pichia pastoris*.

Alternatively, integrative vectors, may be used rather than circular plasmids. Such integrative vectors are disclosed in U.S. Pat. No. 4,882,279, issued Nov. 21, 1989 to James M. Cregg. The '279 patent is also incorporated herein by reference as if fully set forth. Integrative vectors suitable for use with the subject promoters, 3' termination sequences, FLD1 marker genes and expression cassettes comprise a serially arranged sequence of at least a first insertable DNA fragment, a selectable marker gene, and a second insertable DNA fragment. An expression cassette containing a heterologous structural gene is inserted in this vector between the first and second insertable DNA fragments whether before or after the marker gene. Alternatively, an expression cassette can be formed in situ if the FLD promoter is contained within one of the insertable fragments to which the structural gene may be operably linked.

The first and second insertable DNA fragments are each at least about 200 nucleotides in length and have nucleotides sequences which are homologous to portions of the genomic DNA of the species to be transformed. Insertable fragments may be as low as 50 nucleotides in length if a diploid strain of *Pichia pastoris* is used. The various components of the integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are oriented in the parent genome.

Nucleotide sequences useful as the first and second insertable DNA fragments are nucleotide sequences which are homologous with separate portions of the native genomic site at which genomic modification is to occur. For example, if genomic modification is to occur at the locus of the alcohol oxidase gene, the first and second insertable DNA fragments employed would be homologous to separate portions of the alcohol oxidase gene locus. Examples of nucleotide sequences which could be used as first and second insertable DNA fragments are deoxyribonucleotide sequences such as the *Pichia pastoris* alcohol oxidase (AOX1) gene, dihydroxyacetone synthase (DAS1) gene, p40 gene and HIS4 gene. The AOX1 gene, DAS1 gene, p40 gene, and HIS4 genes are disclosed in U.S. Pat. Nos. 4,855,231, and 4,885,242, both incorporated herein by reference. The designatin DAS1 is equivalent to the DAS designation originally used in U.S. Pat. Nos. 4,855,231 and 4,885,242. The first insertable DNA fragment may contain a FLD promoter which FLD promoter is also part of the expression cassette. A second insertable DNA fragment may contain 3' flanking sequence starting about 300 base pairs downstream from the translational stop codon of an FLD gene.

The vectors and chimeric genes of the present invention can be constructed by standard techniques known to one of ordinary skill in the art and found, for example, in Sambrook et al. (1989) in *Molecular Cloning: A Laboratory Manual*, or any of a myriad of laboratory manuals on recombinant DNA technology that are widely available. A variety of strategies are available for ligating fragments of DNA, the choice of which depends on the nature of the termini of the DNA fragments and can be readily determined by the skilled artisan.

When the methylotrophic yeast host cells are transformed with a linear DNA fragment comprising a heterologous gene under the control of the FLD promoter, the expression cassette is integrated into the host cell genome by any of the gene replacement methods known in the art such as by one-step gene replacement. Rothstein, 1983 *Methods Enzymol.* 101:202 and Cregg et al., 1987 *Bio/Technology* 5:479. When the DNA vector is a circular plasmid, such plasmid may be linearized to facilitate integration and then integrated into the methylotrophic yeast genome at the same or different loci by addition. Cregg et al. (1985) *Mol. Cell. Biol.*5 :3376.

The vectors of the present invention may be transformed into the cells of a methylotrophic yeast using known methods such as the spheroplast technique, described by Cregg et al. 1985, or the whole-cell lithium chloride yeast transformation system, Ito et al. *Agric. Biol. Chem.* 48:341, modified for use in Pichia as described in EP 312,934. Other published methods useful for transformation of the plasmids or linear vectors of the present invention include U.S. Pat. No. 4,929,555 to Cregg and Barringer; Hinnen et al. (1978) *Proc. Nat. Acad. Sci.* 75:1929; Ito et al. (1983) *J. Bacteriol.* 153:163; U.S. Pat. No. 4,879,231 to D. W. Stroman et al; Sreekrishna et al. (1987) *Gene* 59:115. Electroporation and PEG1000 whole cell transformation procedures may also be used. Cregg and Russel (1985) *Methods in Molecular Biology: Pichia Protocols*, Chapter 3, Humana Press, Totowa, N.J., pp. 27–39.

In accordance with the present invention, host cells are provided which comprise the subject expression cassettes and expression vectors. The yeast host for transformation may be any suitable methylotrophic yeast. Suitable methylotrophic yeasts include but are not limited to yeast capable of growth on methanol such as yeasts of the genera *Candida, Hansenula, Torulopsis*, and *Pichia*. A list of species which are exemplary of this class of yeasts may be found in C. Anthony (1982), *The Biochemistry of Methylotrophs*, 269. *Pichia pastoris, Pichia methanolica, Pichia anomola, Hansenula polymorpha* and *Candida boidinii* are examples of methylotrophic yeasts useful in the practice of the present invention. Preferred methylotrophic yeasts are of the genus *Pichia*. Especially preferred are *Pichia pastoris* strains GS115 (NRRL Y-15851); GS190 (NRRL Y-18014) disclosed in U.S. Pat. No. 4,818,700; and PPF1 (NRRL Y-18017) disclosed in U.S. Pat. No. 4a812,405. Auxotrophic *Pichia pastoris* strains such as GS115, GS190 and PPF1 are advantageous to the practice of the present invention for their ease of selection. Wild type *Pichia pastoris* strains such as NRRL Y-11430 and NRRL Y-11431 may be employed with equal success if a suitable transforming marker gene is selected, such as the use of SUC2 to transform *Pichia pastoris* to a strain capable of growth on sucrose or if antibiotic resistance marker is employed, such as resistance to G418 and zeocin.

For the large-scale production in *Pichia pastoris* of heterologous proteins using the vectors of the present invention, a two-state, high cell-density, batch fermentation may be employed. During the first stage (growth stage), *Pichia* host cells may be cultured in defined minimal medium with a suitable carbon source such as glycerol or glucose, and a suitable nitrogen source such as ammonium sulfate, ammonium nitrate or other ammonium salt. Ammonium hydroxide may also be used. In this first stage, heterologous gene expression is repressed, which allows cell expansion and generation of cell mass. Once the repressing carbon or nitrogen source is depleted, either methanol or methylamine, or both, are added which initiates expression of the heterologous gene in the second stage (production stage). In accordance with the present invention, induction using both methanol and methylamine provides a synergistic effect. That is, levels of gene expression are higher when both methanol and methylamine are used to induce compared to when methanol alone or methylamine alone is used to induce.

Alternatively, gene expression may be induced using formaldehyde or formate as energy source or choline and other methylated amines as nitrogen source. If methanol is used to induce, it is used in a concentration of 1% or less. Very small amounts, down to almost nothing are all that is needed to induce expression. If formaldehyde is used to induce, an amount of about 10 mM to almost nothing is used, keeping in mind that formaldehyde is very toxic to *P. pastoris* in amounts of 10 mM or higher. Formate is also very toxic to *P. pastoris* in amounts greater than 100 mM. If methylamine, choline or other methylated amines are used to induce gene expression, an amount of 0.5% to almost nothing is used.

The host cells may be grown in the temperature range of about 35 degrees Centigrade (C.) down to 4 degrees C. A preferred temperature for growth of cells is 30 degrees C. The pH range for growth of cells is 2.8 to 7.5 with a preferred ranged of 3.0 to 6.5. Conditions and methodologies for growth of methylotrophic yeast cells are thoroughly discussed in Higgins and Cregg (1998) *Methods in Molecular Biology: Pichia protocols*, Humana Press, Totowa, N.J., and are incorporated herewith as if fully set forth.

Transformed *Pichia pastoris* cells may be selected by using appropriate techniques including but not limited to culturing previously auxotrophic cells after transformation in the absence of the biochemical product required (due to the cell's auxotrophy), selection for and detection of a new phenotype ("methanol slow") or culturing in the presence of an antibiotic which is toxic to the yeast in the absence of a resistance gene contained in the transformant.

As discussed hereinbefore, a subject FLD gene may be used as a selectable marker to transform a methylotrophic yeast cell for purposes of direct selection for formaldehyde resistance. In addition, the present invention provides a method for direct selection of a transformed host cell which comprises introducing into a host cell a vector comprising an FLD coding sequence operably linked to an FLD promoter as defined herein or operably linked to a heterologous promoter. Optimally, the FLD coding sequence is also operably linked at its 3' end to a 3' termination sequence. Transformed host cells are grown in the presence of formaldehyde and resistant cells selected.

Levels of formaldehyde used to select for resistant cells will depend on the yeast strain used as a host cell, and the promoter used to drive expression of the FLD gene. For example, if a wild type *Pichia pastoris* strain and native FLD promoter are used, then a level of about 7 mM formaldehyde is enough to allow for direct selection. If an fld mutant *Pichia pastoris* strain is used with either a native FLD promoter or a heterologous promoter (i.e., a promoter other than the FLD promoter), then a level of about 2 mM is enough to allow for direct selection.

Positive transformants may be characterized by Southern blot analysis (Sambrook et al. 1989) which is particularly useful for identifying the site of DNA integration. Northern analysis (Sambrook et al. 1989) may be used to confirm methanol-responsive and methylamine responsive gene expression. The product of the heterologous gene may also be assayed using well known methodologies and isolates which produce the desired gene product at the appropriate level identified. Immunoblotting using polyclonal or monoclonal antibodies to the product of the heterologous gene may also be used.

Another aspect of the present invention provides a method for directing expression of a heterologous gene in a methylotrophic yeast which comprises introducing into a methylotrophic yeast cell an isolated nucleic acid comprising an FLD promoter isolated from a methylotrophic yeast, which promoter is operably linked at its 3' end to the 5' end of a heterologous gene. Optimally, the heterologous gene is also operably linked at its 3' end to the 5' end of a 3' termination sequence which functions in a methylotrophic yeast. Such an isolated nucleic acid is preferably within a vector which replicates within a methylotrophic yeast or which integrates into the genome of a methylotrophic yeast as hereinbefore described. A methylotrophic yeast cell is transformed with the expression cassette or expression vector and then the cell is grown in a medium having sugar such as glycerol or glucose as carbon source and ammonium hydroxide, ammonium sulfate, ammonium nitrate, or other ammonium salt as nitrogen source. After the repressing carbon or nitrogen source is depleted, expression of the heterologous gene is induced by addition of methanol or methylamine. Alternatively, gene expression may be induced with formaldehyde or formate as energy source or choline and other methylated amines as nitrogen source. Routine methods are used to isolate the heterologous protein from the culture medium (if the heterologous protein is secreted from the host cells) or from the methylotrophic yeast cells (if the heterologous protein is not secreted).

The present invention also provides kits which comprise the expression cassettes and expression vectors of the present invention. In this aspect of the invention, a kit is provided which comprises an expression cassette comprising a subject FLD promoter from a methylotrophic yeast and a 3' termination sequence such as the 3' termination sequence from the AOX1 gene, p40 gene, HIS4 gene or FLD gene. At least one restriction site and preferably a multiple cloning site may be conveniently located between the FLD promoter and 3' termination sequence so that a heterologous gene may be inserted and operably linked to the promoter and 3' termination sequences. The kit may also comprise a vector such as a plasmid which replicates in a methylotrophic yeast or which integrates into the genome of a methylotrophic yeast as hereinbefore described. Preferably, the vector comprises a marker gene and one or more restriction sites for insertion of the expression cassette. Alternatively, the kit may comprise the expression cassette already placed within a vector. In another embodiment, the kit also comprises a yeast strain which may be transformed with the expression vector and transformed cells directly selected. Examples of selectable markers and auxotrophic yeast strains are hereinbefore described. In yet another embodiment of this aspect of the invention, the kit may also contain a control plasmid such as the FLD1 promoter operably linked to a reporter gene such as β-lactamase. Such a plasmid may be supplied alone or within a transformed yeast strain.

The present invention also provides a kit comprising an expression vector with an FLD gene as a selectable marker. The vector may be an autonomous replicating vector or an integrative vector. As herinbefore described, the FLD coding sequence may be under control of the native FLD 5' and/or 3' regulatory sequences or may be operably linked to heterologous 5' and/or 3' regulatory sequences. Also within the expression vector is an expression cassette comprising a promoter which functions in a methylotrophic yeast and a 3' termination sequence which functions in a methylotrophic yeast. Within the expression cassette, between the 5' regulatory sequence and the 3' regulatory sequence are one or more restriction sites so that a heterologous gene may be inserted and placed under the control of the regulatory sequences. In a preferred embodiment, the promoter and 3' termination sequences are from the *Pichia pastoris* AOX1 gene. In another embodiment, the kit further comprises a vector having the above-described expression cassette with a signal sequence operably linked to the 5' regulatory region. Between the end of the signal sequence and 3' termination sequence is located at least one restriction site for insertion of a heterologous gene. Preferably, a multiple cloning site is located between the end of the signal sequence and 5' end of the 3' termination sequence. Examples of appropriate signal sequences include the *Saccharomyces cerevisiae* alpha mating factor pre pro (αmf) and the *Pichia pastoris* acid phosphatase signal sequence (PHO1).

The invention is further illustrated by the following specific examples which are not intended in any way to limit the scope of the invention.

EXAMPLES

The strains, plasmids, and media employed in the following examples have the compositions given below:

The wild-type *P. pastoris* strain used was NRRL Y-11430. *P. pastoris* fld1 mutant strains were generated using nitrosoguanidine and were obtained through Dr. George Speri of Phillips Petroleum Company (Bartlesville, Okla., USA). The *Pichia pastoris* fld1 strain GS241 (fld1-1) was deposited at the Northern Regional Research Center of the U.S. Department of Agriculture (NRRL), Peoria, Ill. on Sep. 20, 1999 and assigned Accession No. NRRL Y-30225. MS105, a *P. pastoris* fld1 his4 strain, was constructed by crossing GS241 (fld1-1) with GS115 (his4). MS105 was also deposited at the NRRL on Sep. 20, 1999 and assigned Accession No. NRRL Y-30226. The plasmids pYG1 and pYG2 have been deposited in at the NRRL on Sep. 20, 1999 and assigned Accession Nos. and NRRL B-30223 and NRRL B-30224, respectively. The *Hansenula polymorpha* strain used was CB54732. Bacterial recombinant DNA manipulations were performed in either *Eseherichia coli* strain MC1061 or DH5. Yeast strains were cultured in a rich YPD medium (1% yeast extract, 2% peptone, 0.4% glucose) or a minimal medium composed of 0.17% yeast nitrogen base without ammonium sulfate and amino acids, a carbon source (0.4% glucose or 0.5% methanol), and a nitrogen source (0.5% ammonium sulfate or 0.25% methylamine chloride). *E. coil* strains were cultured in Luria broth medium supplemented with either 100 μg/ml ampicillin or 50 μg/ml zeocin (Invitrogen Corporation, Carlsbad, Calif., USA) as required.

Example 1

Isolation of Formaldehyde Dehydrogenase-defective Mutants of *P. pastoris*

As a first step in cloning the *P. pastoris* formaldehyde dehydrogenase gene (FLD1), mutants were sought that were specifically defective in FLD activity. Previous biochemical studies of methylotrophic yeasts indicated that FLD is involved in the metabolism of both methanol as carbon source and methylamine as nitrogen source (Zwart et al., 1983). To search for *P. pastoris* fld1 mutants, nitrosoguanidine-mutagenized cultures were screened for strains that were unable to utilize methanol as carbon source and methylamine as nitrogen source. Complementation analysis and other classical genetic techniques were performed as described in Cregg and Russell (1998). Five mutants belonging to a single complementation group were identified.

These five strains were further examined by measuring the levels of activity of key methanol pathway enzymes in extracts prepared from methanol-induced cultures of each strain. These enzymes included: alcohol oxidase (AOX), catalase, dihydroxyacetone synthase, dihydroxyacetone kinase, FLD, and formate dehydrogenase. For enzyme assays, yeast strains were grown in shake flasks at 30° C. in YNB medium (without amino acids and ammonium sulfate, DIFCO) using 0.5% methanol as carbon source and 0.5% ammonium sulfate as nitrogen source. Cultures were harvested in the late logarithmic phase, and cell-free extracts were prepared using glass beads as described in Waterham et al. (1996). The protein concentrations in cell-free extracts were determined using either the method of Bradford (1976) or the Pierce BCA protein assay kit (Rockford, Ill.) with bovine serum albumin as standard. Alcohol oxidase (van der Klei et al., 1990), catalase (Lück, 1963), dihydroxyacetone synthase (Waites and Quayle, 1981), dihydroxyacetone kinase (van Dijken et al., 1978), and formate dehydrogenase (van Dijken, 1976) activities were determined by published methods. Formaldehyde dehydrogenase activity was measured spectrophotometrically by following the rate of NADH formation at 340 nm in the presence of saturating amounts of formaldehyde, glutathione, and NAD as described by Schutte et al. (1976). Reaction mixtures contained 33 mM sodium phosphate buffer (pH 7.9–8.0), 2 mM glutathione, 1 mM NAD, 1 mM formaldehyde, and limiting amounts of enzyme in a final volume of 1.0 ml. The rate of absorbance change at 340 nm was followed for at least 2 min, and activities were calculated by using the constant $\epsilon=6.22$ cm$^2$/nmol for NAD. Alcohol oxidase activities were expressed in μmol/mg/min, and formaldehyde dehydrogenase activities were expressed in μmol/mg/min. β-lactamase activity, expressed as nmol/mg/min, was assayed spectrophotometrically at 569 nm and 30° C. in 25 mM Tris-HCl (pH 7.5) using 11.1 mM PADAC as substrate (extinction coefficient 44.403 cm$^{-1}$M$^{-1}$).

As shown in Table 1, growth of wt *P. pastoris* on methanol as sole carbon source and ammonium sulfate as sole nitrogen source specifically induced high levels of FLD activity (Table 1). Results were essentially the same for each of the five mutants and are shown in Table 1 for one of the mutant strains GS241. Each mutant contained significant levels of activity for all enzymes assayed except FLD which was undetectable. As controls, methanol-grown wild-type *P. pastoris* had normal levels of FLD activity, and methanol-induced cells of a *P. pastoris* strain that is deleted for its AOX genes and as a result cannot grow on methanol also contained substantial levels of FLD activity.

The phenotypic and biochemical characteristics of the mutants were consistent with the finding that they were specifically defective in the *P. pastoris* FLD1 gene. One putative fld1 strain, GS241 (fld1-1), was selected for all further manipulations.

Example 2

Isolation and Characterization of the *P. pastoris* FLD1 Gene

To clone the putative FLD1 gene by functional complementation, strain GS241 was first crossed to *P. pastoris* strain GS115 (his4) to obtain a derivative that was both methanol-utilization defective (Mut$^-$) and auxotrophic for histidine (His$^-$). One Mut$^-$His$^-$ strain that resulted from this cross, MS105 (fld1-1 his4), was then transformed with 5–10 μg of a *P. pastoris* genomic DNA library constructed in the *P. pastoris*-*E. coli* shuttle vector pYM8 using the spheroplast method (Cregg et al., 1985; Liu et al., 1995). The plasmid pYM8 is composed of the *Saccharomyces cerevisiae* histidinol dehydrogenase gene (SHIS4) and a *P. pastoris*-specific autonomous replication sequence (PARS1) inserted into *E. coli* plasmid pBR322. Approximately 50,000 library transformants were selected for His$^+$ prototrophy on YND medium agar and resultant selected clones further selected on YNM plates for Mut$^+$ phenotype. Total DNA was extracted from a pool of several hundred His$^+$ Mut$^+$ colonies and used to transform *E. coli*. One plasmid recovered from this process, pYG1, was able to retransform strain MS105 to both His$^+$ and Mut$^+$ and was examined further.

Figure 2:
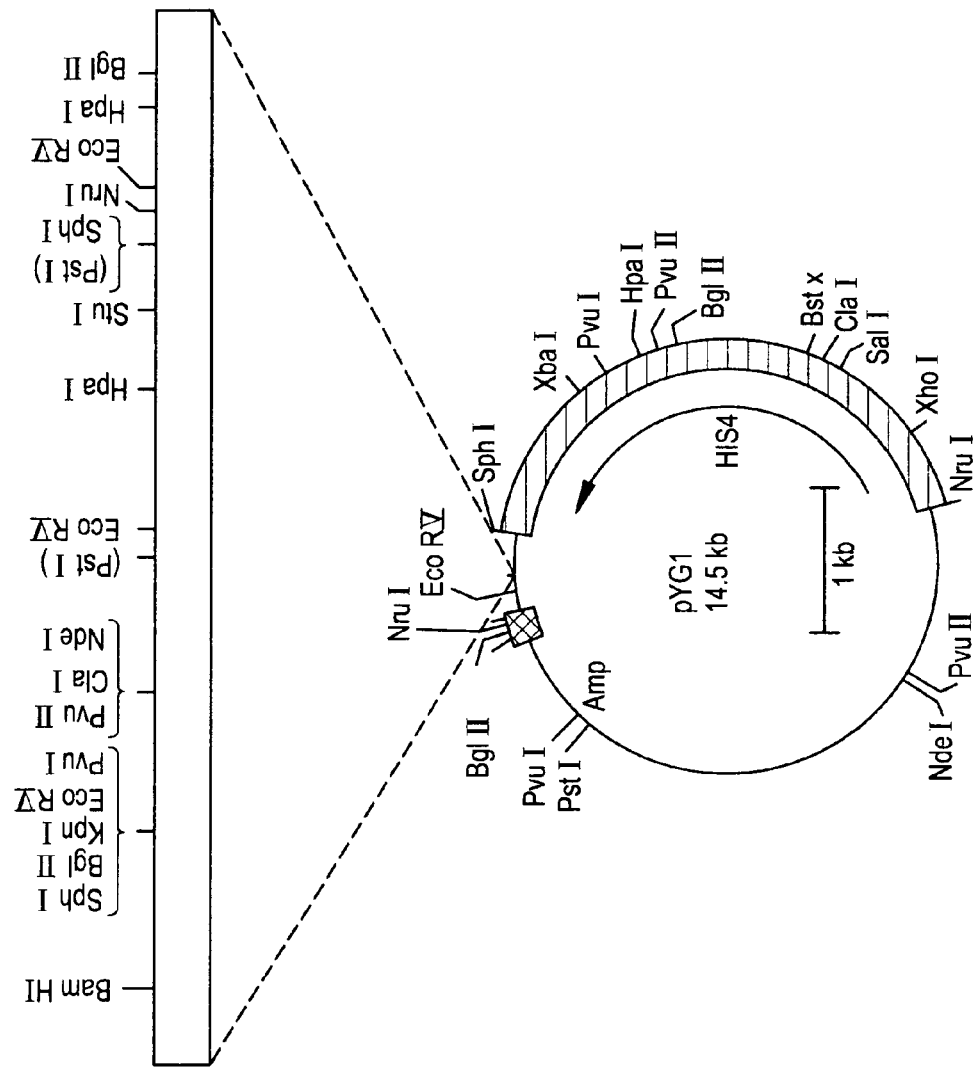
FIG. 2 is a restriction enzyme map of the FLD1 gene-containing vector pYG1.

To determine the location of the putative FLD1 gene on pYG1, the plasmid was restriction mapped, and selected fragments from the vector were subcloned and tested for the ability to complement strain MS105. Recombinant DNA methods were performed essentially as described in Sambrook et al. (1989). Oligonucleotides were synthesized and DNA sequencing was performed at the Oregon Regional Primate Research Center, Molecular Biology Core Facility (Beaverton, Oreg., USA). The plasmid was found to be 14.5 kb in size and to contain an insert of 6.8 kb (FIG. 2). A 2.7-kb SphI-BamHI fragment was found to be sufficient to complement the Mut$^-$ defect in MS105 and was sequenced. The DNA sequence identified a long open reading frame (ORF) whose predicted product had strong similarity to other alcohol dehydrogenases. The sequence also suggested the possible presence of an intron near the 5' terminus of the gene.

Figure 3B:
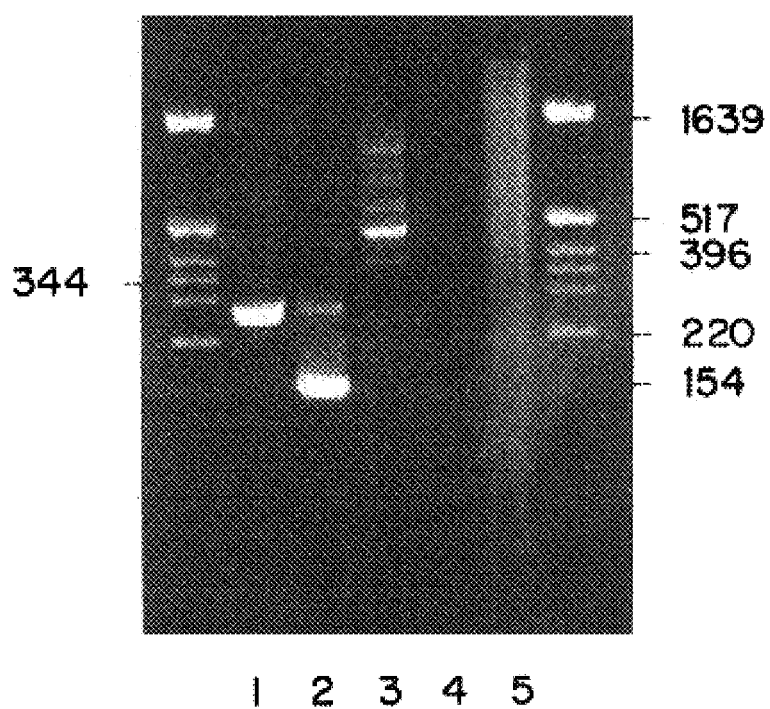
FIG. 3B is an electrophoregram of PCR and RT-PCR reaction products. PCR reactions were performed with the following: lane 1, genomic DNA template plus both primers; lane 2, cDNA template plus both primers; lane 3, cDNA template plus 5' primer only; lane 4, cDNA template plus 3' primer only; lane 5, both primers without DNA template. Flanking marker bands are denoted in base pairs.

To confirm the presence of an intron, this region of the ORF was amplified from mRNA by the reverse transcriptase-polymerase chain reaction method (RT-PCR), and the size and sequence of the product was compared to that obtained by PCR of the genomic fragment on plasmid pYG1 (FIG. 3). PCR reactions were performed as described by Kramer and Coen (1995). Total *P. pastoris* RNA was isolated according to Schmitt et al. (1990). The RT-PCR reaction was performed as previously described (Frohman et al., 1988; Stewart et al., 1992) using the following oligonucleotide primers: 5'-CACAATGTCTACCGAAGGTC-3' (SEQ ID NO:7) (5' primer) and 5'-CCAGAAAGCGTG-TAAGCATCAG-3' (SEQ ID NO:8) (3' primer).

Whereas the genomic product was 284 bp in length, the cDNA product was significantly shorter at 170 bp. Alignment of the cDNA and genomic sequences demonstrated that a segment of 114 bp that was present in the genomic DNA was absent from the cDNA. Furthermore, examination of the putative intron/exon junctions revealed typical yeast splice junctions (5' junction, 5'-GTAAGT-3"; 3' junction, 5'-YAG-3") and branch point (5'-TACTAAC-3') (Domdey et al., 1984; Sasnauskas et al., 1992). A single intron is therefore present at this position in the ORF. Finally, Southern blots of selected restriction digests of wild-type genomic DNA, using a fragment from the ORF as hybridization probe, indicated that the *P. pastoris* genome contained only one copy of the gene.

The DNA and predicted amino acid sequences of the ORF are shown in FIGS. 4A–4B. The sequence data are available from EMBL/GenBank/DDBJ under accession number AF066054. The ORF is 1,137 bp long and is predicted to encode a protein of 379 amino acids with a calculated molecular mass of 39,870. The intron begins at a position 18 bp (six amino acids) 3' of the A of the predicted methiomne initiator ATG and is 114 bp in length. Northern blots of total RNA extracted from glucose- and methanol-grown wild-type *P. pastoris* cells, using a DNA fragment from the ORF region, showed a single mRNA species of approximately 1.3 kb that was present at high levels in methanol- but not glucose-grown cells (data not shown). Overall, the codon usage of the putative FLD1 gene was typical of other highly expressed *P. pastoris* genes (Sreekrishna, 1993).

The GenBank/NCBI database was searched for other proteins with amino acid sequence similarity to the ORF product. The sequence of the putative FLD1 protein (Fld1p) showed the highest identity (71%) with that of glutathione-dependent formaldehyde dehydrogenase from the yeast *Candida maltosa* (Sasnauskas et al., 1992) (FIG. 5). *C. maltosa* is an n-alkane assimilating yeast and FLD is believed to be important in protecting the yeast from the toxic effects of formaldehyde (Sasnauskas et al., 1992). The close similarity of the predicted *C. maltosa* FLD product to that of the cloned ORF provides further support that this ORF encodes *P. pastoris* Fld1p. The *P. pastoris* Fld1p sequence also showed high identity with alcohol dehydrogenase III (ADHIII) proteins of higher eukaryotes (65%, human; 63%, horse; 64%, rat) and a lower but significant identity with other higher eukaryotic ADHs (Holmquist and Vallee, 1991; Koivusalo et al., 1998; Rathnagiri et al., 1998). Finally, the Fld1p sequence showed little similarity with the predicted amino acid sequences of *S. cerevisiae* ADHs. The closest, at 19% identity, was *S. cerevisiae* ADHI (Jornvall et al., 1987).

Example 3

Isolation and Characterization of the *Hansenula polymorpha* FLD Gene

Figure 9:
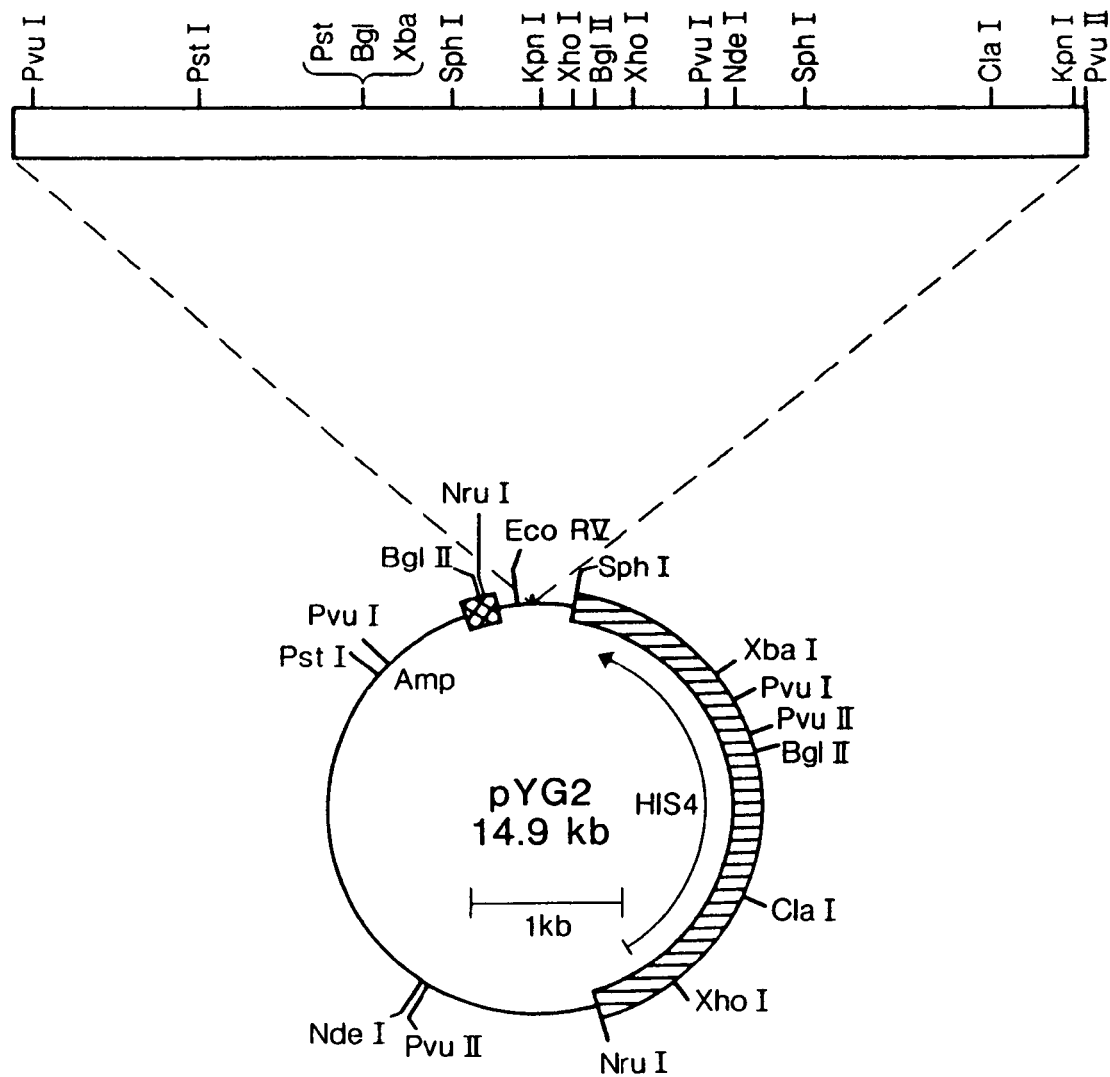
FIG. 9 is a restriction enzyme map of the *Hansenula polymorpha* FLD gene-containing vector pYG2.
Figure 11:
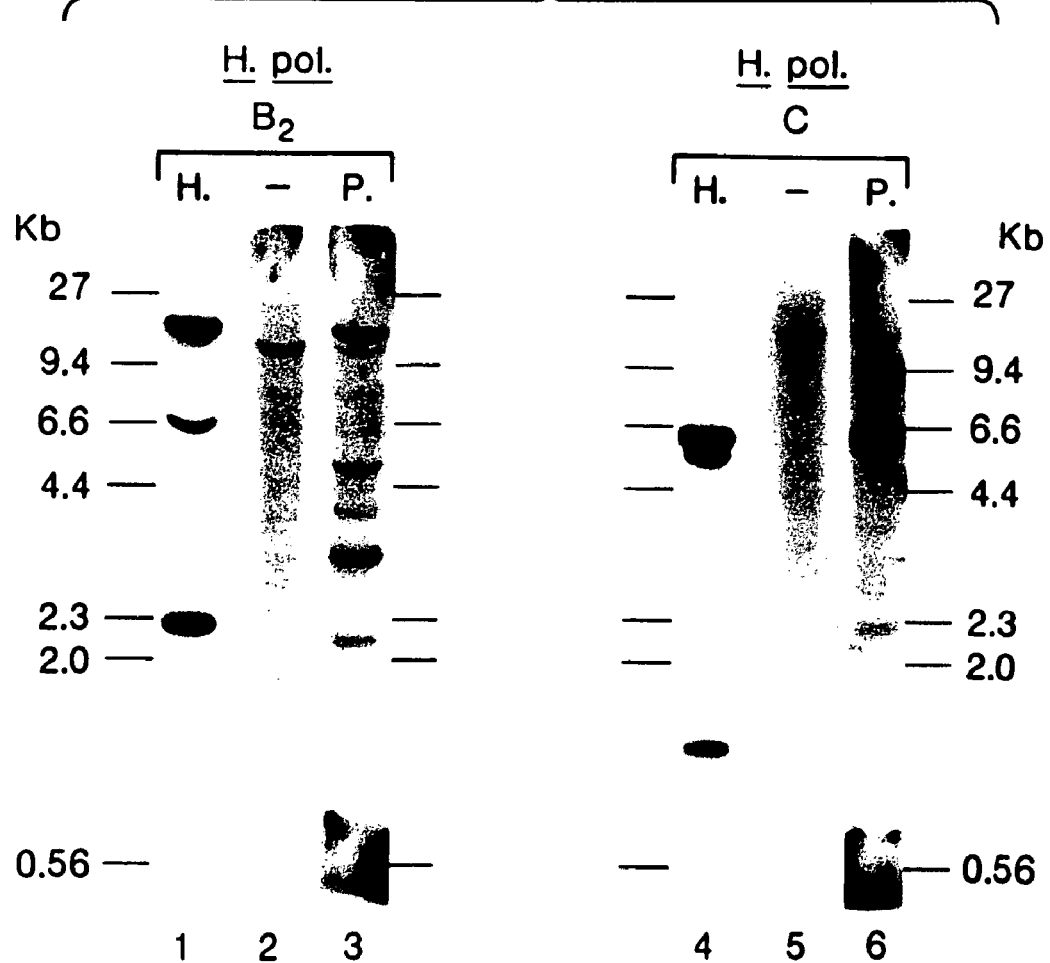
FIG. 11 is a Southern blot showing genomic DNA from *H. polymorpha* digested with either BglII(B2) (lanes 1–3) or ClaI (C) (lanes 4–6) and hybridized with the following probes: pYG2 (lanes 1 and 4), pYM8(lanes 2 and 5), or pYG1 (lanes 3 and 6).

The putative *H. polymorpha* FLD1 gene was isolated using the same functional complementation strategy described above for the *P. pastoris* gene. An *H. polymorpha* genomic DNA library was constructed in *P. pastoris* vector pYM8 in the same manner as the *P. pastoris* library (Liu et al. 1995). Briefly, *H. polymorpha* genomic DNA was partially digested with Sau3A and size selected for fragments of 5–20 kb. These fragments were ligated into the BamHI site of pYM8. The library was composed of approximately 100,000 independent *E. coli* transformants with greater than 90% containing an insert. The average size of insert DNA was approximately 10 kb. Assuming that the size of the *H. polymorpha* genome is 10,000 kb, the library contained approximately 100 genome equivalents of *H. polymorpha* genomic DNA. Plasmids were recovered and analyzed for ones that were capable of simultaneously retransforming MS105 (fld1-1 his4 to both His$^+$ and Mut$^+$ phenotypes. One plasmid, pYG2, (FIG. 9) that met these criteria was selected for use in these studies. This plasmid contained an *H. polymorpha* DNA insert of 7.2 kb and the Mut complementing activity was found to reside within a 2.4-kb SphI fragment (FIG. 10). Southern blot studies indicated that vectors pYG1 and pYG2 contained homologous FLD genes. An example of such a blot is shown in FIG. 11. In this experiment, genomic DNA from *H. polymorpha* was digested with either BglII (B$_2$) (lanes 1–3) or ClaI (C) (lanes 4–6) and hybridized with the following labeled probes: pYG2 (lanes 1 and 4), pYM8 (lanes 2 and 5), or pYG1 (lanes 3 and 6). The pYG2 probe containing the putative *H. polymorpha* FLD1 gene produced major bands of ~15 kb and ~7 kb when hybridized at high stringency to BglII and ClaI digested *H. polymorpha* genomic DNAs, respectively. Hybridization of pYG1 containing the *P. pastoris* FLD1 gene at low stringency (30% formamide, 37° C. hybridization, 1× SSC, room temperature washing) produced major bands of hybridization of the same size. These bands were not due to hybridization of vector sequences from pYM8, since the pYM8 probe showed no major bands of hybridization with *H. polymorpha* genomic DNA under the same low stringency conditions.

Example 4

Comparison of the Thermal Stability of Fld1p from *P. pastoris* and *H. polymorpha*

Further evidence that the cloned *P. pastoris* gene actually encodes an FLD was obtained by comparing the thermal stability of its product to FLD from *H. polymorpha*. *H. polymorpha* is a related methylotrophic yeast that has a significantly higher optimal growth temperature than *P. pastoris* (42° C. versus 30° C.). FLD from *H. polymorpha* would therefore be expected to display a significantly higher thermal stability than *P. pastoris* FLD. A comparison of the thermal stability properties of the putative FLDs from the two yeasts provides strong support for the identity of the gene product. In this experiment, the putative *P. pastoris* and *H. polymorpha* FLD1 genes were expressed in methanol-grown cells of the *P. pastoris* fld1-1 his4 strain MS105, and the thermal stability of FLD activity in each was assessed by incubating extracts prepared from the strains at 60° C. for selected periods of time and determining the rate of loss of FLD activity. If the genes actually encode Fld1p, the FLD inactivation rate for *H. polymorpha* Fld1p expressed in *P. pastoris* should be similar to that of wild-type *H. polymorpha* Fld1p, and the inactivation rate for the *P. pastoris* gene product should be similar to that of wild-type *P. pastoris* Fld1p.

Figure 6:
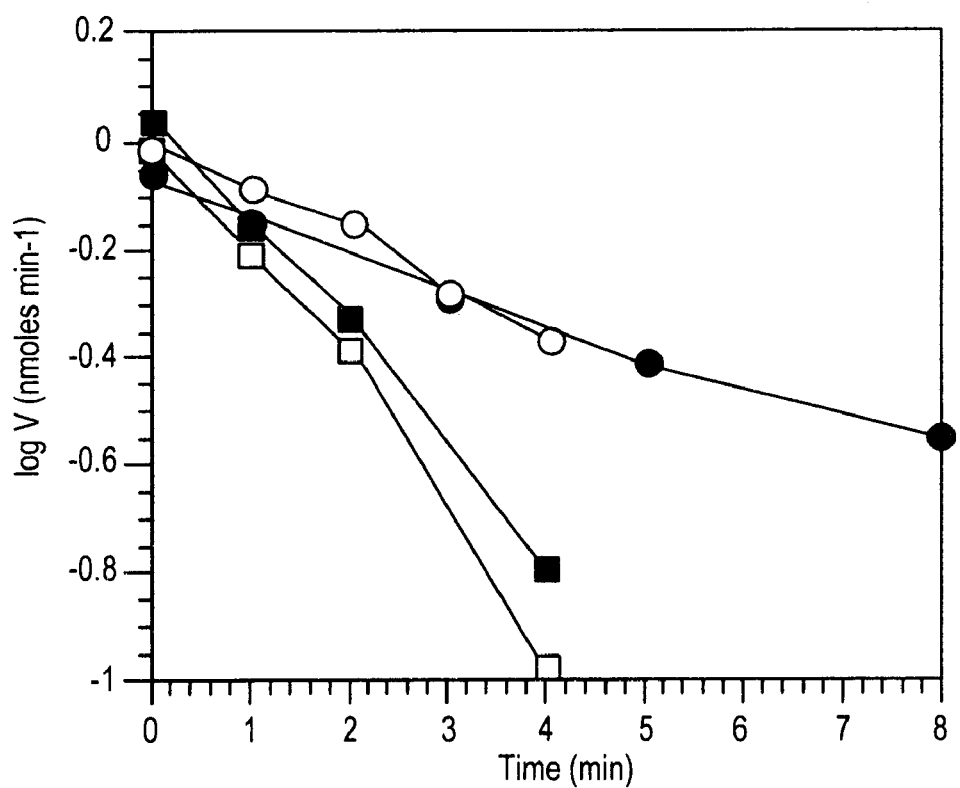
FIG. 6 graphically depicts thermal stability of formaldehyde dehydrogenase activities in *P. pastoris* strains transformed with putative FLD1 genes from *P. pastoris* and *H. polymorpha*. Strains shown are: wild-type *P. pastoris* (■); wild-type *H. polymorpha* (●); *P. pastoris* MS105 (pYG1) (□); and *P. pastoris* MS105 (pYG2) (○).

To perform this comparison, it was first necessary to establish that the thermal stability of the *P. pastoris* and *H. polymorpha* FLDs were significantly different and to clone the putative *H. polymorpha* FLD1 gene. Thermal stabilities were determined by preparing cell-free extracts from methanol-grown cultures of wild-type *P. pastoris* and *H. polymorpha* and incubating them at 60° C.; At selected times during incubation, samples of extract were removed and assayed for FLD activity. As shown in FIG. 6, *H. polymorpha* FLD activity was significantly more heat stable than *P. pastoris* activity.

Thermal stability of FLD expressed from *H. polymorpha* vector pYG2 was then compared to that of FLD from the *P. pastoris* vector pYG1. As shown in FIG. 6, FLD in MS105 (pYG2) had a thermal inactivation rate similar to that of wild-type *H. polymorpha*, while MS105(pYG1) had a rate similar to that of *P. pastoris*. These results, taken with results demonstrating the specific absence of FLD activity in *P. pastoris* strain GS241 (and MS105) and the close similarity of the primary amino acid sequences of the cloned *P. pastoris* ORF and *C. maltosa* FLD, indicated that the cloned ORF encoded *P. pastoris* Fld1p.

Example 5

Analysis of P$_{FLD1}$ and Comparison to P$_{AOX1}$

Figure 1:
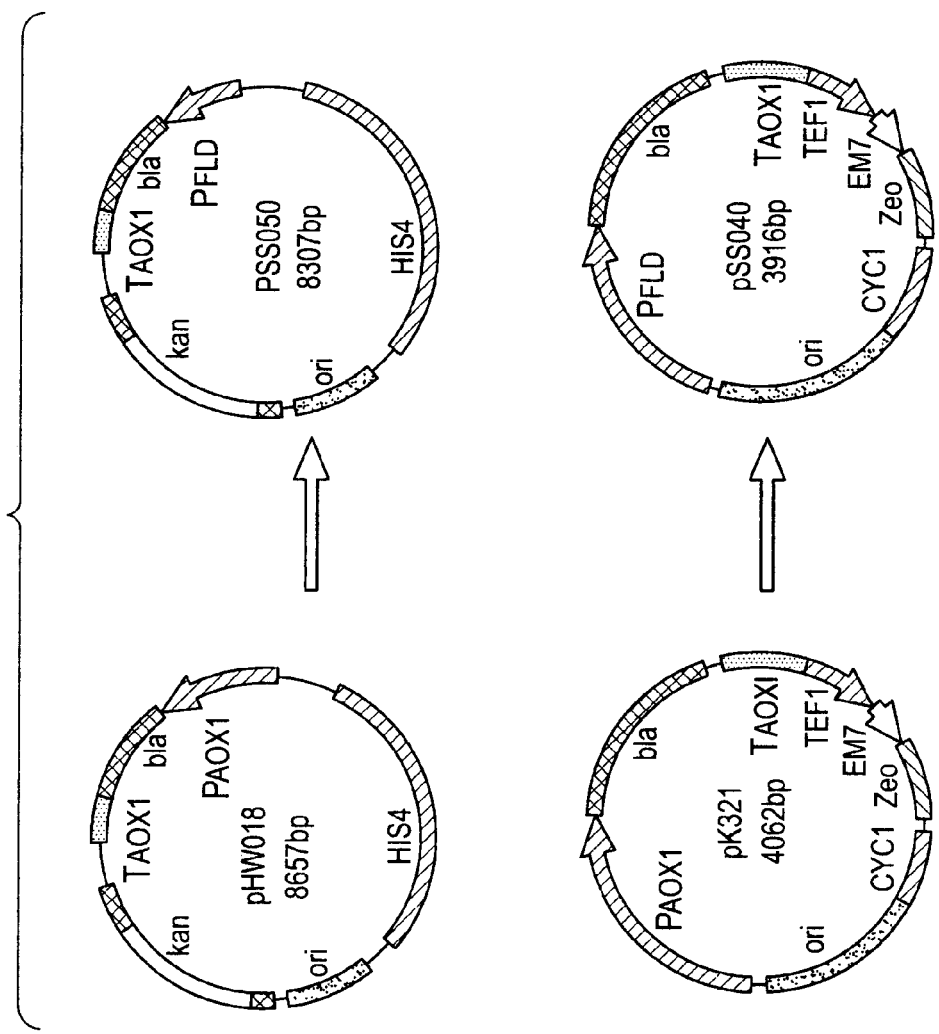
FIG. 1 provides physical maps of selected plasmids pHW018, pSS050, pK321, and pSS040.

To examine gene expression under the transcriptional control of P$_{FLD1}$, two vectors were constructed (FIG. 1).

Both vectors contained identical expression cassettes composed of a 0.6-kb MunI-BamHI fragment with sequences originating from just 5' of the methionine initiator ATG codon of FLD1 fused to the bacterial bla gene encoding β-lactamase (β-lac), followed by a fragment containing the AOX1 transcriptional terminator. The MunI is artificial and was installed by PCR using an oligonucleotide that contained the MunI site along with sequences from just 5' of the methionine initiator ATG of FLD1. A restriction site at this location was needed to aid in inserting the promoter 5' of the β-lactamase reporter gene. A MunI site was chosen because the DNA termini generated with MunI are compatible with EcoRI and there was an EcoRI site already present just 5' of the β-lactamase reporter in the test vectors. An EcoRI site could not be placed at the 3' end of the FLD1 gene because the FLD1 promoter region has a natural EcoRI site.

One vector, pSS040, contained a unique NsiI restriction site within the $P_{FLD1}$ fragment. When cut at this site and transformed into *P. pastoris*, the vector efficiently integrated at the $P_{FLD1}$ locus. The result of this integration event was a $P_{FLD1}$-bla expression cassette that also included native FLD1 sequences upstream of the $P_{FLD1}$ fragment (WT-$P_{FDL1}$-bla) Assuming that all sequences required for transcriptional control of FLD1 are located 5' of the FLD1 ORF, regulation of bla and FLD1 expression in this strain should be nearly identical. As shown in Table 2, this appeared to be true in that the relative levels of β-lac and FLD activity in the strain were similar in cells grown in four expression test media. These four media contained as carbon and nitrogen sources, respectively: (1) glucose and ammonium sulfate (G/$NH_4^+$),(2) glucose and methylamine (G/MA), (3) methanol and ammonium sulfate (M/$NH_4^+$), and (4) methanol and methylamine (M/MA). As expected, β-lac and FLD activities were highly repressed in cells grown on G/$NH_4^+$ medium. Cells grown on either G/MA or M/$NH_4^+$ media contained at least ten-fold more β-lac and FLD with the highest level of both enzymes observed in cells grown in M/MA medium.

The second vector, pSS050, contained the *P. pastoris* HIS4 gene as the selectable marker. When cut at a unique SalI site within HIS4 and transformed in *P. pastoris*, this vector efficiently integrated at the *P. pastoris* HIS4 locus. The result of this integration event was a $P_{FLD1}$-bla expression-cassette with sequences from pBR322 just 5" of the 0.6-kb $P_{FLD1}$ fragment (pB-$P_{FLD1}$-bla). Comparison of β-lac activity levels in this strain with those observed in the WT-$P_{FLD1}$-bla strain allowed evaluation of whether the 0.6-kb fragment contained all upstream regulatory sequences required for normal regulation. Table 2 shows that β-lac activity levels in the pB-$P_{FLD1}$-bla strain were approximately two-fold higher than those observed in the WT-$P_{FLD1}$-bla, strain when grown in each of the four expression test media. These results indicated that most sequences required for normal regulation were present within the $P_{FLD1}$ fragment but that sequences that constitutively repress $P_{FLD1}$ by a factor of about two-fold existed somewhere 5' of the $P_{FLD1}$ fragment and were missing from the 0.6-kb fragment.

Finally, levels of β-lac activity produced under control of $P_{FLD1}$ were compared with those of a strain in which bla expression was under the transcriptional control of $P_{AOX1}$ (Waterham et al., 1997). As previously reported, $P_{AOX1}$ expression is strongly repressed in the glucose-containing media and is highly and specifically induced in methanol-containing media (Tschopp et al., 1987; Waterham et al., 1997) (Table 2). Comparable levels of β-lac were present in cells of the WT-$P_{FLD1}$-bla strain grown in either M/$NH_4^+$ or M/MA media, whereas cells of the pB-$P_{FLD1}$-bla strain contained levels of β-lac that were significantly higher than those in the $P_{AOX1}$-bla strain. Especially noteworthy were the levels of β-lac in the pB-$P_{FLD1}$-bla strain on M/$NH_4^+$ and M/MA media which were consistently about twice those observed in the $P_{AOX1}$-bla strain on the same media.

Example 6

The FLD1 Gene Confers Resistance to Formaldehyde

The *P. pastoris* FLD1 gene was incorporated into pPICZ vectors containing Zeo$^R$ (Invitrogen, Carlsbad, Calif.). Two such pPICZ-FLD1 vectors were constructed. In one, the whole FLD1 gene including the FLD1 promoter, structural gene and transcriptional terminator were inserted (pP$_{FLD1}$-FLD1) In the other, the FLD1 structural gene (and transcriptional terminator) was placed under the control of the *P. pastoris* glyceraldehyde-3-phosphate dehydrogenase gene (GAP) promoter (pP$_{GAP}$-FLD1). These two plasmids were linearized within their respective promoter fragments ($P_{FLD1}$, $P_{GAP}$) and transformed by electroporation into wild-type and MS105 (fld1-1 his4) *P. pastoris* strains by selection for resistance to Zeocin at 100 μg/ml and 1 mg/ml. The lower Zeocin concentration selects for *P. pastoris* transformants that have one integrated copy of a Zeo$^R$ vector while the high Zeocin concentration selects for transformants that have multiple integrated Zeo$^R$ vector copies. Selected transformants of each type were streaked onto a YPD medium plate containing either Zeocin at 100 mg/ml or 1 mg/ml and onto sets of YPD plates containing formaldehyde at concentrations ranging from 0 to 30 mm. As a control, wild-type and GS241 strains transformed with a pPICZ vector alone (i.e., without an FLD1 gene) were also streaked onto the plates.

It was observed that MS105 strains transformed with pPICZ alone were resistant to 1 mM formaldehyde. MS105-derived strains containing a single copy of pP$_{FLD1}$-FLD1 and p$_{PGAP}$-FLD1 were resistant to 10 mM and 5 mM formaldehyde, respectively, whereas MS105-derived strains containing multiple copies of pP$_{FLD1}$-FLD1 and pP$_{GAP}$-FLD1 were resistant to 30 mM and 10 mM formaldehyde, respectively. Thus, either the pP$_{FLD1}$-FLD1 and pP$_{GAP}$-FLD1 vectors conferred increased resistance to formaldehyde. In addition, an additive effect was evident in that increased numbers of copies of each vector resulted in an increased level of resistance to formaldehyde over that conferred by one copy of each vector.

Wild-type *P. pastoris* strains transformed with pPICZ alone were resistant to 5 mM formaldehyde. Because wild-type strains contain one native copy of the FLD1 gene, the concentration of formaldehyde to which this strain was resistant was significantly higher as expected. Wild-type-derived strains containing a single copy of pP$_{FLD1}$-FLD1 and pP$_{GAP}$-FLD1 were resistant to 10 and 5 mM formaldehyde, respectively, whereas wild-type-derived strains containing multiple copies of pP$_{FLD1}$-FLD1 and pP$_{GAP}$-FLD1 were resistant to 30 mM formaldehyde, respectively. Thus, the pP$_{FLD1}$-FLD1 but not the pP$_{GAP}$-FLD1 vectors conferred increased resistance to formaldehyde. An additive effect was also evident with increased numbers of copies of each vector conferring an increased level of resistance to formaldehyde over one copy of each vector.

These transformation experiments were repeated with the pP$_{FLD1}$-FLD1 and pP$_{GAP}$-FLD1 vectors and wild-type and MS105 *P. pastoris* strains only selecting directly for resistance to formaldehyde (along with selection for Zeocin resistance as a control). With strain MS105, 2 mM formaldehyde was optimal for selection of transformants. This concentration of formaldehyde produced approximately the same number of transformants as observed with the 100 μg/ml Zeocin selection control. For wild-type *P. pastoris*, 7 mM formaldehyde was optimal for selection of transformants with the $pP_{FLD1}$-FLD1 vector. This concentration produced approximately the same number of transformants as observed with the 100 μg/ml Zeocin selection control. Transformation was not observed with the $pP_{GAP}$-FLD1 vector.

Based on these positive results, a *P. pastoris* expression vector was constructed. The vector contains a heterologous gene expression cassette composed of DNA fragments containing the AOX1 promoter and transcriptional terminator separated by a multiple cloning site (MCS) into which heterologous genes can be inserted. The expression cassette is followed by a DNA segment containing the $P_{GAP}$-FLD1 gene construct, and this segment is followed by a DNA fragment that is derived from sequences 3' of the AOX1 gene. This set of DNA fragments is inserted into the bacterial plasmid pBluesceipt (Stratagene, San Diego, Calif.) so that the vector can be propagated in *E. coli*.

After insertion of the heterologous gene at the MCS, the resulting vector is cut with the restriction enzyme NotI to release from the bacterial plasmid a DNA fragment capable of transforming *P. pastoris*. The fragment is transformed into either wild-type or MS105 (fld1-1) strains of *P. pastoris* by electroporation and transformants are selected on YPD medium plates containing either 7 mM formaldehyde for wild type strains or 2 mM for MS105 fld1 strains. The vector fragment will insert itself into the *P. pastoris* genome in one of two ways. The first is by a gene replacement event replacing the AOX1 gene. In addition to increased resistance to formaldehyde, such gene replacement transformants can be easily identified phenotypically because of their very slow growth rate on methanol due to the absence of the AOX1 gene.

Another way the vector will insert itself into the *P. pastoris* genome involves the circularization of the transforming fragment at some point before integration. After circularization, the transforming DNA can integrate by a single cross-over event at any of the *P. pastoris* genomic loci represented in the vector. These genomic regions include the FLD1, AOX1 promoter and AOX1 3' flanking loci. Integration at any of these sites produces no change in strain phenotype other than increased resistance to formaldehyde. It is important to note that integration of this fragment in any manner does not result in the incorporation of an antibiotic resistance gene or any other gene foreign to *P. pastoris* with the exception of the heterologous gene whose protein product is desired.

REFERENCES

Bradford, M. (1976) A rapid and sensitive method for the quantitation of microgram quantities of protein utilizing the principle of protein-dye binding. Anal. Biochem. 72, 248–254.

Cregg, J. M. Expression in the methylotrophic yeast *Pichia pastoris*. (1998) In: J. Fernandez and J. Hoeffler (Eds.), Nature: The Palette for the Art of Expression, Chapter 10. Academic Press, San Diego, in press.

Cregg, J. M., Barringer, K. J., Hessler, A. Y. and Madden, K. R. (1985) *Pichia pastoris* as a host system for transformations. Mol. Cell. Biol. 5, 3376.

Cregg, J. M. and Russell, K. A. Transformation. (1998) In: D. R. Higgins and J. M. Cregg (Eds.) Methods in Molecular Biology: Pichia Protocols, Chapter 3. Humana Press, Totowa, N.J., pp. 27–39.

Domdy, H., Apostol, B., Lin, R. J., Newman. A., Brody, E. and Abelson, J. (1984) Lariat structures are in vivo intermediates in yeast pre-mRNA splicing. Cell 39, 611–621.

Frohman, M. A., Dush, M. K. and Martin, G. R. (1988) Rapid production of full-length cDNAs from rare transcripts: amplification using a single gene-specific oligonucleotide primer. Proc. Natl. Acad. Sci. USA. 85, 8998–9002.

Higgins, D. R. and Cregg, J. M. (1998) Methods in Molecular Biology: Pichia Protocols. Humana Press, Totowa, N.J.. pp. 1–15.

Holmquist, B. and Vallee, B. L. (1991) Human liver class III alcohol and glutathione dependent formaldehyde dehydrogenase are the same enzyme. Biochem. Biophys. Res. Commun. 178, 1371–1377.

Jornvall, H., Persson, B. and Jeffery, J. (1987) Characteristics of alcohol/polyol dehydrogenases: the zinc-containing long-chain alcohol dehydrogenases Eur. J. Biochem. 167, 195–201.

Koivusalo, M., Barmann, M. and Uotila, L. (1989) Evidence for the identity of glutathione-dependent formaldehyde dehydrogenase and class III alcohol dehydrogenase. FEBS Lett. 257, 105–109.

Kramer, M. F. and Coen, D. M. The polymerase chain reaction. (1995) In: F. M. Ausubel, R. Brent, R. E. Kingston, D. D. Moore, J. G. Seidman, J. A. Smith and K. Struhl (Eds.) Current Protocols in Molecular Biology, Vol. 2, Chapter 15. John Wiley and Sons, New York, pp. 15.1.1–15.1.9.

Liu, H., Tan, X, Russell, K. A., Veenhuis, M. and Cregg, J. M. (1995) PER3, a gene required for peroxisome biogenesis in *Pichia pastoris*, encodes a peroxisomal membrane protein involved in protein import. J. Biol. Chem. 270, 10940–10951.

Lück, H. Catalase. (1963) In: H. U. Bergmeyer (Ed.), Methods of Enzymatic Analysis, Academic Press, San Diego, pp. 885–894.

Rathnagiri, P., Krug, J. F., Kozak, C., Moretti, T., O'Brien, S. J., Seuanez, H. N. and Goldman, D. (1989) Cloning and comparative mapping of human class III alcohol dehydrogenase cDNA. Biochem. Biophys. Res. Commun. 164, 453–460.

Sambrook, J., Fritsch, E. F. and Maniatis, T. (1989) Molecular Cloning: A Laboratory Manual, 2nd Edn. Cold Spring Harbor Laboratory Press, Cold Spring Harbor, N.Y. Sasnauskas, K., Jomantiene, R., Januska, A., Lebediene, E., Lebedys, J. and Janulaitis, A. (1992) Cloning and sequencing analysis of a *Candida maltosa* gene which confers resistance to formaldehyde in *Saccharomyces cerevisiae*. Gene 122, 207–211.

Schmitt, M., Brown, T. A. and Trumpower, B. L. (1990) A rapid and simple method for preparation of RNA from *Saccharomyces cerevisiae*. Nucleic Acids Res. 18, 3091–3092.

Schutte, H., Flossdorf, J., Sahm, H. and Kula, M. R. (1976) Purification and properties of formaldehyde dehydrogenase and formate dehydrogenase from *Candida boidinii*. Eur. J. Biochem. 62, 151–160.

Sibirny, A. A., Ubiyvovk, V. M., Gonchar, M. V., Titorenko, V. I., Voronovsky, A. Y., Kapultsevich, Y. G. and Bliznik, K. M. (1990) Reactions of direct formaldehyde oxidation to $CO_2$ are non-essential for energy supply of yeast methylotrophic growth. Arch. Microbiol 154, 566–575.

Sreekrishna, K. Strategies for optimizing protein expression and secretion in the methylotrophic yeast *Pichia pastoris*. (1993) In: R. H. Baltz, G. D. Hegeman, and P. L. Skatrud (Eds.), Industrial Microorganisms: Basic and Applied Molecular Genetics. American Society for Microbiology, Washington, D.C., pp. 119–126.

Stewart, P., Kersten, P., Wymelenberg, A. V., Gaskell, J. and Cullen, D. (1992) Lignin peroxidase gene family of *Phanerochaete chrysosporium*: complex regulation by carbon and nitrogen limitation and identification of a second dimorphic chromosome. J. Bacteriol. 174, 5036–5042.

Tschopp, J. F., Brust, P. F., Cregg, J. M., Stillman, C. A. and Gingeras, T. R. (1987) Expression of the lacZ gene from two methanol-regulated promoters in *Pichia pastoris*. Nucleic Acids Res. 15, 3859–3876.

van Dijken, J. P., Harder, W., Beardsmore, A. J. and Quayle, J. R. (1978) Dihydroxyacetone: an intermediate in the assimilation of methanol by yeasts? FEMS Microbiol. Lett. 4, 97–102.

van Dijken, J. P. (1976) Oxidation of methanol by *Hansenula polymorpha*: purification and kinetic properties of methanol oxidase. Ph.D. Thesis, University of Groningen, pp. 30–43.

van der Klei, I. J., Bystrykh, L. V. and Harder, W. (1990) Alcohol oxidase from *Hansenula polymorpha* CBS 4732. Methods Enzymol. 188, 420–422.

Veenhuis, M., van Dijken, J. P. and Harder, W. (1983) The significance of peroxisomes in the metabolism of one-carbon compounds in yeasts. Adv. Microb. Physiol. 24, 1–82.

Waites, M. J. and Quayle, J. R. (1981) The interrelation between transketolase and dihydroxyacetone synthase activities in the methylotrophic yeast *Candida boidinii*. J. Gen. Microbiol. 124, 309–316.

Waterham, H. R., Keizer-Gunnink, I., Goodman, J. M., Harder, W. and Veenhuis, M. (1992) Development of multi-purpose peroxisomes in *Candida boidinii* grown in oleic acid-methanol limited continuous cultures. J. Bacteriol 174, 4057–4063.

Waterham, H. R., Digan, M. E., Koutz, P. J., Lair, S. V. and Cregg, J. M. (1997) Isolation of the *Pichia pastoris* glyceraldehyde-3-phosphate dehydrogenase gene and regulation and use of its promoter. Gene 186, 37–44.

Zwart, K., Veenhuis, M., van Dijken, J. P. and Harder, W. (1980) Development of amine oxidase-containing peroxisomes in yeast during growth on glucose in the presence of methylamine as the sole source of nitrogen. Arch. Microbiol. 126, 117–126.

TABLE 1

Relative enzyme activity levels in methanol-utilization-detective mutants of *P. pastoris*.

| | % Activity[a] | | | | | |
|---|---|---|---|---|---|---|
| Strain | AOX | CAT | FLD | FDH | DAS | DAK |
| WT (methanol-) | 100 | 100 | 100 | 100 | 100 | 100 |
| WT (glucose) | 0 | 2 | 1 | 0 | 3 | 53 |
| KM7121 (aox1 aox2) | 0 | 100 | 26 | 31 | ND[b] | 88 |
| GS241 (fld1) | 20 | 178 | 0 | 46 | 58 | 64 |

[a]Activity for each enzyme is expressed as a percentage of that observed in extracts prepared from methanol-grown cultures of wild-type *P. pastoris*. Abbreviations are: AOX, alcohol oxidase; CAT, catalase; FLD, formaldehyde dehydrogenase; FDH, formate dehydrogenase; DAS, dihydroxyacetone synthase; DAK, dihydroxyacetone kinase.
[b]Not determined.

TABLE 2

Comparison of β-lactamase activity in extracts of *P. pastoris* strains expressing bla under control of $P_{FLD}$ and $P_{AOX1}$.

| | Source of:[a] | | Enzyme activity[b] | | | |
|---|---|---|---|---|---|---|
| Strain | C | N | β-lactamase | | FLD | |
| WT-$P_{FLD1}$-bla (at FLD1 locus) | G | $NH_4^+$ | 14 | (4%) | 0.13 | (6%) |
| | G | MA | 168 | (48%) | 1.50 | (69%) |
| | M | $NH_4^+$ | 310 | (88%) | 1.69 | (78%) |
| | M | MA | 352 | (100%) | 2.16 | (100%) |
| pB-$P_{FLD1}$-bla (at HIS4 locus) | G | $NH_4^+$ | 19 | (5%) | 0.11 | (5%) |
| | G | MA | 357 | (102%) | 0.82 | (38%) |
| | M | $NH_4^+$ | 529 | (150%) | 1.48 | (69%) |
| | M | MA | 530 | (151%) | 1.75 | (81%) |
| $P_{AOX1}$-bla | G | $NH_4^+$ | 0.3 | (0.1%) | 0.12 | (6%) |
| | G | MA | 0.5 | (0.1%) | 0.65 | (30%) |
| | M | $NH_4^+$ | 241 | (68%) | 1.40 | (65%) |
| | M | MA | 254 | (72%) | 2.06 | (95%) |

[a]Each strain was grown in media containing either glucose (G) or methanol (M) as carbon source and ammonium sulfate ($NH_4^+$) or methylamine (MA) as nitrogen source.
[b]β-lactamase activities are expressed as nmol/mg per min and, in parentheses, as a percentage of activity seen in the WT-$P_{FLD1}$-bla strain grown on methanol and methylamine. Activities represent the mean of three experiments using two independently transformed strains.

What is claimed is:

1. An isolated nucleic acid comprising the sequence set forth in SEQ ID NO: 1 or SEQ ID NO: 5.

2. A vector comprising the isolated nucleic acid of claim 1.

3. A host cell comprising the vector of claim 2.

4. The host cell of claim 3 wherein the host cell is a bacterial cell or yeast cell.

* * * * *

UNITED STATES PATENT AND TRADEMARK OFFICE
CERTIFICATE OF CORRECTION

PATENT NO. : 7,250,502 B2  Page 1 of 1
APPLICATION NO. : 10/459970
DATED : July 31, 2007
INVENTOR(S) : James M. Cregg It is certified that error appears in the above-identified patent and that said Letters Patent is hereby corrected as shown below:

Column 1, line 16, delete the following text:
"and the U.S. National Science Foundation (MCB-9514289)"

Signed and Sealed this

Twenty-sixth Day of January, 2010

David J. Kappos
*Director of the United States Patent and Trademark Office*

SEQUENCE LISTING

<160> NUMBER OF SEQ ID NOS: 8

<210> SEQ ID NO 1
<211> LENGTH: 2774
<212> TYPE: DNA
<213> ORGANISM: Pichia pastoris
<220> FEATURE:
<221> NAME/KEY: CDS
<222> LOCATION: (598)..(615)

<220> FEATURE:
<221> NAME/KEY: CDS
<222> LOCATION: (730)..(1851)

<400> SEQUENCE: 1

```
gcatgcagga atctctggca cggtgctaat ggtagttatc aacggagct gaggtagtcg      60
atatatctgg atatgccgcc tataggataa aaacaggaga gggtgaacct tgcttatggc    120
tactagattg ttcttgtact ctgaattctc attatgggaa actaaactaa tctcatctgt    180
gtgttgcagt actattgaat cgttgtagta tctacctgga gggcattcca tbaattagtg    240
agataacaga gttgggtaac tagagagaat aatagacgta tgcatgatta ctacacaacg    300
gatgtcgcac tctttcctta gttaaaacta tcatccaatc acaagatgcg ggctggaaag    360
acttgctccc gaaggataat cttctgcttc tatctcccttt cctcatatgg tttcgcaggg    420
ctcatgcccc ttcttccttc gaactgcccg atgaggaagt ccttagccta tcaaagaatt    480
cgggaccatc atcgattttt agagccttac ctgatcgcaa tcaggatttc actactcata    540
taaatacatc gctcaaagct ccaactttgc ttgttcatac aattcttgat attcaca       597
```

| atg tct acc gaa ggt caa | gtaagttcaa tcaaagtaat tgtttgggag | 645 |
|---|---|---|
| Met Ser Thr Glu Gly Gln | | |
| 1               5 | | |

| ggaagaagat tgttttattg cgaacctttc aatatcttac ccgactaaat aaccattaca | 705 |
|---|---|

| gtgaatttt tactaactat atag atc atc aaa tgt aag gca gct gtt gcc | 756 |
|---|---|
| Ile Ile Lys Cys Lys Ala Ala Val Ala | |
| 10                    15 | |

| tgg gag gca gga aag gat ctc tct att gag gag att gag gtt ctt cct | 804 |
|---|---|
| Trp Glu Ala Gly Lys Asp Leu Ser Ile Glu Glu Ile Glu Val Leu Pro | |
|      20                  25                  30 | |

| cca aga gcc cat gaa gtt aga gtg aaa gtg gaa ttc act ggt gta tgc | 852 |
|---|---|
| Pro Arg Ala His Glu Val Arg Val Lys Val Glu Phe Thr Gly Val Cys | |
|          35                  40                  45 | |

| cac act gat gct tac acg ctt tct ggt gca gat gca gag gga agt ttc | 900 |
|---|---|
| His Thr Asp Ala Tyr Thr Leu Ser Gly Ala Asp Ala Glu Gly Ser Phe | |
|     50                  55                  60 | |

| cct gtt gtg ttc ggc cat gaa ggt gct ggt gtt gtc gag tca gtt gga | 948 |
|---|---|
| Pro Val Val Phe Gly His Glu Gly Ala Gly Val Val Glu Ser Val Gly | |
| 65                  70                  75 | |

| gaa ggt gtt gag tcc gtg aag gtt ggg gat tct gta gtg ctt ctg tac | 996 |
|---|---|
| Glu Gly Val Glu Ser Val Lys Val Gly Asp Ser Val Val Leu Leu Tyr | |
| 80                  85                  90                  95 | |

| act cct gag tgc aga gag tgc aag ttc tgt ctg tct ggt aag acg aac | 1044 |
|---|---|
| Thr Pro Glu Cys Arg Glu Cys Lys Phe Cys Leu Ser Gly Lys Thr Asn | |
|             100                 105                 110 | |

| ctc tgt ggt aaa atc aga gcc acc cag ggt aaa ggt ttg tta cca gac | 1092 |
|---|---|
| Leu Cys Gly Lys Ile Arg Ala Thr Gln Gly Lys Gly Leu Leu Pro Asp | |
|         115                 120                 125 | |

| ggg act tct cgt ttc cgt tgt aag ggc aag gat ttg ttt cac tat atg | 1140 |
|---|---|
| Gly Thr Ser Arg Phe Arg Cys Lys Gly Lys Asp Leu Phe His Tyr Met | |
|     130                 135                 140 | |

| gga tgt tct tcc ttt tct caa tac act gtg gtg gct gac atc tca gtg | 1188 |
|---|---|
| Gly Cys Ser Ser Phe Ser Gln Tyr Thr Val Val Ala Asp Ile Ser Val | |
| 145                 150                 155 | |

| gtt aaa gtc caa gac gaa gct cct aag gac aag aca tgt ctg ttg ggt | 1236 |
|---|---|
| Val Lys Val Gln Asp Glu Ala Pro Lys Asp Lys Thr Cys Leu Leu Gly | |
| 160                 165                 170                 175 | |

| tgt ggt gtt acc aca ggg tac ggt gct gct atc aac act gct aag atc | 1284 |
|---|---|
| Cys Gly Val Thr Thr Gly Tyr Gly Ala Ala Ile Asn Thr Ala Lys Ile | |
|             180                 185                 190 | |

```
tct aag ggt gac aag atc ggt gtg ttt ggt gct gga tgt att gga tta      1332
Ser Lys Gly Asp Lys Ile Gly Val Phe Gly Ala Gly Cys Ile Gly Leu
        195                 200                 205 tct gtc atc caa ggt gca gtt tcc aaa ggt gca agc gag att att gta      1380
Ser Val Ile Gln Gly Ala Val Ser Lys Gly Ala Ser Glu Ile Ile Val
    210                 215                 220 att gac atc aat gat tca aag aag gca tgg gcg gac caa ttt ggt gca      1428
Ile Asp Ile Asn Asp Ser Lys Lys Ala Trp Ala Asp Gln Phe Gly Ala
    225                 230                 235 act aag ttt gtc aat cct aca acc tta cca gaa ggt acc aat att gtt      1476
Thr Lys Phe Val Asn Pro Thr Thr Leu Pro Glu Gly Thr Asn Ile Val
240                 245                 250                 255 gac tac ttg att gat atc act gac gga ggc ttt gac tat acc ttc gac      1524
Asp Tyr Leu Ile Asp Ile Thr Asp Gly Gly Phe Asp Tyr Thr Phe Asp
                260                 265                 270 tgt acc ggt aat gtt caa gta atg aga aat gca ctt gaa tct tgc cac      1572
Cys Thr Gly Asn Val Gln Val Met Arg Asn Ala Leu Glu Ser Cys His
            275                 280                 285 aag ggt tgg ggt gag tcg atc atc atc ggt gtc gct gct gct ggt aaa      1620
Lys Gly Trp Gly Glu Ser Ile Ile Ile Gly Val Ala Ala Ala Gly Lys
        290                 295                 300 gaa atc tct acc cgt cct ttc cag ttg gtt act ggc aga gtc tgg aga      1668
Glu Ile Ser Thr Arg Pro Phe Gln Leu Val Thr Gly Arg Val Trp Arg
    305                 310                 315 gga tgc gcc ttt gga ggt atc aag gga cgt act caa atg cca tct ttg      1716
Gly Cys Ala Phe Gly Gly Ile Lys Gly Arg Thr Gln Met Pro Ser Leu
320                 325                 330                 335 gtt cag gac tat ctt gat ggt aag att aaa gtt gac gag ttt atc aca      1764
Val Gln Asp Tyr Leu Asp Gly Lys Ile Lys Val Asp Glu Phe Ile Thr
                340                 345                 350 cac aga cat gac ctg gac aac atc aac aaa gca ttt cat gac atg cat      1812
His Arg His Asp Leu Asp Asn Ile Asn Lys Ala Phe His Asp Met His
            355                 360                 365 gct gga aac tgt att cgt gct gtg att act atg cac taa gtacgacgta       1861
Ala Gly Asn Cys Ile Arg Ala Val Ile Thr Met His
        370                 375 tgatgaatga atgagttatg taaggcccga tctcagctag gacgtttata gacctatgta    1921
tatatatgta tgtatacgta tatacctcaa actcatttta tggctatagg aaggattgtt    1981
ttcatcgtta tgtccgaaga tacatcaata cagcgtttct tgatttgtac caaacactcc    2041
ccaggtagat tctccagtct cgctagttac cttcgcggta ttgatcgacg ctctgtgaaa    2101
aaataaaaaa aaaatgtcaa tagtatcgag gttggcttca aaatcaccag cgttctgtat    2161
cgggttccgt ttttgagctt ctactttcct tatatccatc atacattcct gtgcttgaat    2221
tcagcagtag aatgtccgat cgatatattg tgttgcatat caacaccacc gccaatgaga    2281
gttctcagca gttcaaacgc gacccttcag agattattga ctagcatgg gttctgctag     2341 atcctggaac caactttgaa atagttggta ggggaagtgt tctggctaaa ccattcaaca    2401
ctcctataac cccgctttgt accagcatga caactcttac atgggaaagt gtcaagaacg    2461
ctggttcact caaggatgcg ctagaggagc ttagcagatt tattgactca aacttggtca    2521
gcaacggctt gtcattcagt tttataactc tgaatgcctg ggatctccgc ttgaaattac    2581
ccaaggagtc gcgtgaaaga agtatagccc ttcccgcgta cttggactta cccaagtact    2641
ttgatcttag aaaagaattc tgtagatggg cccaaaaatc atctgcattg actacaaacg    2701
gtaatcacat gagtttagct tatatggtat ctaaacttga aacagaagct agtttggttt    2761
```

-continued tggacgagga tcc 2774

<210> SEQ ID NO 2
<211> LENGTH: 379
<212> TYPE: PRT
<213> ORGANISM: Pichia pastoris

<400> SEQUENCE: 2

```
Met Ser Thr Glu Gly Gln Ile Ile Lys Cys Lys Ala Ala Val Ala Trp
  1               5                  10                  15
Glu Ala Gly Lys Asp Leu Ser Ile Glu Ile Glu Val Leu Pro Pro
             20                  25                  30
Arg Ala His Glu Val Arg Val Lys Val Glu Phe Thr Gly Val Cys His
             35                  40                  45
Thr Asp Ala Tyr Thr Leu Ser Gly Ala Asp Ala Glu Gly Ser Phe Pro
         50                  55                  60
Val Val Phe Gly His Glu Gly Ala Gly Val Val Glu Ser Val Gly Glu
 65                  70                  75                  80
Gly Val Glu Ser Val Lys Val Gly Asp Ser Val Val Leu Leu Tyr Thr
                 85                  90                  95
Pro Glu Cys Arg Glu Cys Lys Phe Cys Leu Ser Gly Lys Thr Asn Leu
            100                 105                 110
Cys Gly Lys Ile Arg Ala Thr Gln Gly Lys Gly Leu Leu Pro Asp Gly
            115                 120                 125
Thr Ser Arg Phe Arg Cys Lys Gly Lys Asp Leu Phe His Tyr Met Gly
        130                 135                 140
Cys Ser Phe Ser Gln Tyr Thr Val Val Ala Asp Ile Ser Val Val
145                 150                 155                 160
Lys Val Gln Asp Glu Ala Pro Lys Asp Lys Thr Cys Leu Leu Gly Cys
                165                 170                 175
Gly Val Thr Thr Gly Tyr Gly Ala Ala Ile Asn Thr Ala Lys Ile Ser
            180                 185                 190
Lys Gly Asp Lys Ile Gly Val Phe Gly Ala Gly Cys Ile Gly Leu Ser
        195                 200                 205
Val Ile Gln Gly Ala Val Ser Lys Gly Ala Ser Glu Ile Ile Val Ile
    210                 215                 220
Asp Ile Asn Asp Ser Lys Lys Ala Trp Ala Asp Gln Phe Gly Ala Thr
225                 230                 235                 240
Lys Phe Val Asn Pro Thr Thr Leu Pro Glu Gly Thr Asn Ile Val Asp
                245                 250                 255
Tyr Leu Ile Asp Ile Thr Asp Gly Gly Phe Asp Tyr Thr Phe Asp Cys
            260                 265                 270
Thr Gly Asn Val Gln Val Met Arg Asn Ala Leu Glu Ser Cys His Lys
        275                 280                 285
Gly Trp Gly Glu Ser Ile Ile Gly Val Ala Ala Gly Lys Glu
    290                 295                 300
Ile Ser Thr Arg Pro Phe Gln Leu Val Thr Gly Arg Val Trp Arg Gly
305                 310                 315                 320
Cys Ala Phe Gly Gly Ile Lys Gly Arg Thr Gln Met Pro Ser Leu Val
                325                 330                 335
Gln Asp Tyr Leu Asp Gly Lys Ile Lys Val Asp Glu Phe Ile Thr His
            340                 345                 350
Arg His Asp Leu Asp Asn Ile Asn Lys Ala Phe His Asp Met His Ala
        355                 360                 365
```

Gly Asn Cys Ile Arg Ala Val Ile Thr Met His
    370             375

<210> SEQ ID NO 3
<211> LENGTH: 597
<212> TYPE: DNA
<213> ORGANISM: Pichia pastoris

<400> SEQUENCE: 3

| | |
|---|---|
| gcatgcagga atctctggca cggtgctaat ggtagttatc aacggagct gaggtagtcg | 60 |
| atatatctgg atatgccgcc tataggataa aaacaggaga gggtgaacct tgcttatggc | 120 |
| tactagattg ttcttgtact ctgaattctc attatgggaa actaaactaa tctcatctgt | 180 |
| gtgttgcagt actattgaat cgttgtagta tctacctgga gggcattcca tgaattagtg | 240 |
| agataacaga gttgggtaac tagagagaat aatagacgta tgcatgatta ctacacaacg | 300 |
| gatgtcgcac tctttcctta gttaaaacta tcatccaatc acaagatgcg ggctggaaag | 360 |
| acttgctccc gaaggataat cttctgcttc tatctcccct cctcatatgg tttcgcaggg | 420 |
| ctcatgcccc ttcttccttc gaactgcccg atgaggaagt ccttagccta tcaaagaatt | 480 |
| cgggaccatc atcgattttt agagccttac ctgatcgcaa tcaggatttc actactcata | 540 |
| taaatacatc gctcaaagct ccaactttgc ttgttcatac aattcttgat attcaca | 597 |

<210> SEQ ID NO 4
<211> LENGTH: 300
<212> TYPE: DNA
<213> ORGANISM: Pichia pastoris

<400> SEQUENCE: 4

| | |
|---|---|
| gtacgacgta tgatgaatga atgagttatg taaggcccga tctcagctag gacgtttata | 60 |
| gacctatgta tatatatgta tgtatacgta tatacctcaa actcattta tggctatagg | 120 |
| aaggattgtt ttcatcgtta tgtccgaaga tacatcaata cagcgtttct tgatttgtac | 180 |
| caaacactcc ccaggtagat tctccagtct cgctagttac cttcgcggta ttgatcgacg | 240 |
| ctctgtgaaa aaataaaaaa aaaatgtcaa tagtatcgag gttggcttca aaatcaccag | 300 |

<210> SEQ ID NO 5
<211> LENGTH: 1254
<212> TYPE: DNA
<213> ORGANISM: Pichia pastoris
<220> FEATURE:
<221> NAME/KEY: CDS
<222> LOCATION: (1)..(18)
<223> OTHER INFORMATION: genomic, double stranded
<220> FEATURE:
<221> NAME/KEY: CDS
<222> LOCATION: (133)..(1254)
<223> OTHER INFORMATION: genomic, double stranded

<400> SEQUENCE: 5

| | |
|---|---|
| atg tct acc gaa ggt caa gtaagttcaa tcaaagtaat tgtttgggag | 48 |
| Met Ser Thr Glu Gly Gln | |
|  1               5 | |
| ggaagaagat tgttttattg cgaacctttc aatatcttac ccgactaaat aaccattaca | 108 |
| gtgaattttt tactaactat atag atc atc aaa tgt aag gca gct gtt gcc | 159 |
|                         Ile Ile Lys Cys Lys Ala Ala Val Ala | |
|                              10              15 | |
| tgg gag gca gga aag gat ctc tct att gag gag att gag gtt ctt cct | 207 |
| Trp Glu Ala Gly Lys Asp Leu Ser Ile Glu Glu Ile Glu Val Leu Pro | |
|     20                 25                  30 | |

-continued

| | |
|---|---|
| cca aga gcc cat gaa gtt aga gtg aaa gtg gaa ttc act ggt gta tgc<br>Pro Arg Ala His Glu Val Arg Val Lys Val Glu Phe Thr Gly Val Cys<br>35                    40                    45 | 255 |
| cac act gat gct tac acg ctt tct ggt gca gat gca gag gga agt ttc<br>His Thr Asp Ala Tyr Thr Leu Ser Gly Ala Asp Ala Glu Gly Ser Phe<br>50                    55                    60 | 303 |
| cct gtt gtg ttc ggc cat gaa ggt gct ggt gtt gtc gag tca gtt gga<br>Pro Val Val Phe Gly His Glu Gly Ala Gly Val Val Glu Ser Val Gly<br>65                    70                    75 | 351 |
| gaa ggt gtt gag tcc gtg aag gtt ggg gat tct gta gtg ctt ctg tac<br>Glu Gly Val Glu Ser Val Lys Val Gly Asp Ser Val Val Leu Leu Tyr<br>80                    85                    90                    95 | 399 |
| act cct gag tgc aga gag tgc aag ttc tgt ctg tct ggt aag acg aac<br>Thr Pro Glu Cys Arg Glu Cys Lys Phe Cys Leu Ser Gly Lys Thr Asn<br>100                  105                110 | 447 |
| ctc tgt ggt aaa atc aga gcc acc cag ggt aaa ggt ttg tta cca gac<br>Leu Cys Gly Lys Ile Arg Ala Thr Gln Gly Lys Gly Leu Leu Pro Asp<br>115                  120                125 | 495 |
| ggg act tct cgt ttc cgt tgt aag ggc aag gat ttg ttt cac tat atg<br>Gly Thr Ser Arg Phe Arg Cys Lys Gly Lys Asp Leu Phe His Tyr Met<br>130                  135                140 | 543 |
| gga tgt tct tcc ttt tct caa tac act gtg gtg gct gac atc tca gtg<br>Gly Cys Ser Ser Phe Ser Gln Tyr Thr Val Val Ala Asp Ile Ser Val<br>145                  150                155 | 591 |
| gtt aaa gtc caa gac gaa gct cct aag gac aag aca tgt ctg ttg ggt<br>Val Lys Val Gln Asp Glu Ala Pro Lys Asp Lys Thr Cys Leu Leu Gly<br>160                  165                170                175 | 639 |
| tgt ggt gtt acc aca ggg tac ggt gct gct atc aac act gct aag atc<br>Cys Gly Val Thr Thr Gly Tyr Gly Ala Ala Ile Asn Thr Ala Lys Ile<br>180                  185                190 | 687 |
| tct aag ggt gac aag atc ggt gtg ttt ggt gct gga tgt att gga tta<br>Ser Lys Gly Asp Lys Ile Gly Val Phe Gly Ala Gly Cys Ile Gly Leu<br>195                  200                205 | 735 |
| tct gtc atc caa ggt gca gtt tcc aaa ggt gca agc gag att att gta<br>Ser Val Ile Gln Gly Ala Val Ser Lys Gly Ala Ser Glu Ile Ile Val<br>210                  215                220 | 783 |
| att gac atc aat gat tca aag aag gca tgg gcg gac caa ttt ggt gca<br>Ile Asp Ile Asn Asp Ser Lys Lys Ala Trp Ala Asp Gln Phe Gly Ala<br>225                  230                235 | 831 |
| act aag ttt gtc aat cct aca acc tta cca gaa ggt acc aat att gtt<br>Thr Lys Phe Val Asn Pro Thr Thr Leu Pro Glu Gly Thr Asn Ile Val<br>240                  245                250                255 | 879 |
| gac tac ttg att gat atc act gac gga ggc ttt gac tat acc ttc gac<br>Asp Tyr Leu Ile Asp Ile Thr Asp Gly Gly Phe Asp Tyr Thr Phe Asp<br>260                  265                270 | 927 |
| tgt acc ggt aat gtt caa gta atg aga aat gca ctt gaa tct tgc cac<br>Cys Thr Gly Asn Val Gln Val Met Arg Asn Ala Leu Glu Ser Cys His<br>275                  280                285 | 975 |
| aag ggt tgg ggt gag tcg atc atc atc ggt gtc gct gct gct ggt aaa<br>Lys Gly Trp Gly Glu Ser Ile Ile Ile Gly Val Ala Ala Ala Gly Lys<br>290                  295                300 | 1023 |
| gaa atc tct acc cgt cct ttc cag ttg gtt act ggc aga gtc tgg aga<br>Glu Ile Ser Thr Arg Pro Phe Gln Leu Val Thr Gly Arg Val Trp Arg<br>305                  310                315 | 1071 |
| gga tgc gcc ttt gga ggt atc aag gga cgt act caa atg cca tct ttg<br>Gly Cys Ala Phe Gly Gly Ile Lys Gly Arg Thr Gln Met Pro Ser Leu<br>320                  325                330                335 | 1119 |
| gtt cag gac tat ctt gat ggt aag att aaa gtt gac gag ttt atc aca<br>Val Gln Asp Tyr Leu Asp Gly Lys Ile Lys Val Asp Glu Phe Ile Thr<br>340                  345                350 | 1167 |

```
cac aga cat gac ctg gac aac atc aac aaa gca ttt cat gac atg cat    1215
His Arg His Asp Leu Asp Asn Ile Asn Lys Ala Phe His Asp Met His
            355                 360                 365 gct gga aac tgt att cgt gct gtg att act atg cac taa                1254
Ala Gly Asn Cys Ile Arg Ala Val Ile Thr Met His
            370                 375
```

<210> SEQ ID NO 6
<211> LENGTH: 381
<212> TYPE: PRT
<213> ORGANISM: Candida maltosa

<400> SEQUENCE: 6

```
Met Ser Glu Ser Thr Val Gly Lys Pro Ile Thr Cys Lys Ala Ala Val
 1               5                  10                  15

Ala Trp Glu Ala Ala Lys Pro Leu Ser Ile Glu Asp Val Thr Val Ala
                20                  25                  30

Pro Pro Lys Arg His Glu Val Arg Ile Lys Leu Tyr Asp Thr Gly Val
            35                  40                  45

Cys His Thr Asp Ala Tyr Thr Leu Ser Gly Val Asp Pro Glu Gly Ala
        50                  55                  60

Phe Pro Val Ile Leu Gly His Glu Gly Ala Gly Ile Val Glu Ser Ile
 65                  70                  75                  80

Gly Glu Gly Val Thr Asn Val Lys Val Gly Asp His Val Ile Ala Leu
                85                  90                  95

Tyr Thr Pro Glu Cys Gly Glu Cys Lys Phe Cys Lys Ser Gly Lys Thr
            100                 105                 110

Asn Leu Cys Gly Lys Ile Arg Ala Thr Gln Gly Lys Gly Val Met Pro
        115                 120                 125

Asp Gly Thr Ser Arg Phe Thr Cys Lys Gly Lys Glu Ile Leu His Phe
    130                 135                 140

Met Gly Cys Ser Thr Phe Ser Gln Tyr Thr Val Val Ala Asp Ile Ser
145                 150                 155                 160

Val Val Ala Ile Asn Pro Lys Ala Glu Phe Asp Lys Ala Cys Leu Leu
                165                 170                 175

Gly Cys Gly Ile Thr Thr Gly Tyr Gly Ala Ala Thr Ile Thr Ala Asn
            180                 185                 190

Val Gln Lys Gly Asp Asn Val Ala Val Phe Gly Gly Gly Ile Val Gly
        195                 200                 205

Leu Ser Val Ile Gln Gly Cys Ala Glu Arg Gly Ala Ala Gln Ile Ile
    210                 215                 220

Leu Val Asp Ile Ser Asp Lys Lys Glu Glu Trp Gly Gln Lys Leu Gly
225                 230                 235                 240

Ala Thr Ala Phe Val Asn Pro Thr Lys Leu Pro Glu Gly Thr Thr Ile
                245                 250                 255

Val Asp Lys Leu Ile Glu Met Thr Asp Gly Gly Cys Asp Phe Thr Phe
            260                 265                 270

Asp Cys Thr Gly Asn Val Gly Val Met Arg Asn Ala Leu Glu Ala Cys
        275                 280                 285

His Lys Gly Trp Gly Thr Ser Val Ile Ile Gly Val Ala Ala Ala Gly
    290                 295                 300

Lys Glu Ile Ser Thr Arg Pro Phe Gln Leu Val Thr Gly Arg Thr Trp
305                 310                 315                 320

Lys Gly Ala Ala Phe Gly Gly Val Lys Gly Arg Ser Gln Leu Pro Gly
                325                 330                 335
```

```
Ile Val Asn Asn Tyr Leu Asp Gly Lys Leu Lys Val Glu Glu Phe Ile
            340                 345                 350

Thr His Arg Glu Pro Leu Ala Ala Ile Asn Lys Ala Phe Glu Glu Met
        355                 360                 365

His Ala Gly Asp Cys Ile Arg Ala Val Val Asp Leu Ser
    370                 375                 380

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Synthetic
      primer

<400> SEQUENCE: 7
cacaatgtct accgaaggtc                                                  20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Synthetic
      primer

<400> SEQUENCE: 8
ccagaaagcg tgtaagcatc ag                                               22
```